(12) United States Patent
Fang et al.

(10) Patent No.: US 12,004,543 B2
(45) Date of Patent: Jun. 11, 2024

(54) SALT-REDUCED FERMENTATION METHOD FOR HIGH-SALT DILUTE-STATE FERMENTED SOY SAUCE

(71) Applicant: Jiangnan University, Wuxi (CN)

(72) Inventors: Fang Fang, Wuxi (CN); Guangyao Hu, Wuxi (CN); Guocheng Du, Wuxi (CN); Jian Chen, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 151 days.

(21) Appl. No.: 17/540,528

(22) Filed: Dec. 2, 2021

(65) Prior Publication Data

US 2022/0087295 A1    Mar. 24, 2022

(30) Foreign Application Priority Data

Oct. 20, 2021    (CN) .......................... 202111221297.0

(51) Int. Cl.
 A23L 27/50    (2016.01)
 C12N 1/20    (2006.01)
 C12R 1/07    (2006.01)

(52) U.S. Cl.
 CPC .............. *A23L 27/50* (2016.08); *C12N 1/205* (2021.05); *A23V 2002/00* (2013.01); *C12R 2001/07* (2021.05)

(58) Field of Classification Search
 CPC ..... A23L 27/50; C12N 1/205; C12R 2001/07; A23V 2002/00
 USPC ............................................................ 426/18
 See application file for complete search history.

(56) References Cited

PUBLICATIONS

CN 112852667 A—English Abstract. (Year: 2021).*
KR 2110995 B1—English Abstract (Year: 2020).*

* cited by examiner

*Primary Examiner* — Hamid R Badr
(74) *Attorney, Agent, or Firm* — IPRO, PLLC; Na Xu

(57) ABSTRACT

The present disclosure discloses a salt-reduced fermentation method for high-salt dilute-state fermented soy sauce, and belongs to the technical field of fermentation engineering. The present disclosure separates and screens *Weissella paramesenteroides* JL-5 and *Bacillus amyloliquefaciens* JDF-2 which inhibit the growth of spoilage bacteria from low-salt soy sauce mash, and by changing the microbial fermentation process of high-salt dilute-state soy sauce, the strains obtained by screening are used for the fermentation of low-salt soy sauce mash. Without changing the flavor and quality of soy sauce, low-salt fermentation of the soy sauce is enabled to proceed normally, and the biogenic amine content is less than 100 mg $L^{-1}$, and the number of spoilage bacteria in the soy sauce are reduced. The prepared low-salt soy sauce has an amino acid nitrogen content of greater than 1.2 g·100 $mL^{-1}$, contents of various spoilage bacteria of less than $1.0×10^3$ CFU·$g^{-1}$, a NaCl concentration of no more than 10 g·100 $mL^{-1}$, and a sodium content of less than or equal to 420 mg·10 $mL^{-1}$. Without the addition of preservatives, the quality stability is the same as that of soy sauce without salt reduction.

10 Claims, 13 Drawing Sheets

Specification includes a Sequence Listing.

SALT-REDUCED FERMENTATION METHOD FOR HIGH-SALT DILUTE-STATE FERMENTED SOY SAUCE

REFERENCE TO SEQUENCE LISTING

The instant application contains a Sequence Listing in XML format as a file named "YGHY -2021-79.txt", created on Dec. 14, 2023, of 6450 bytes in size, and which is hereby incorporated by reference in its entirety.

TECHNICAL FIELD

The present disclosure relates to a salt-reduced fermentation method for high-salt dilute-state fermented soy sauce, and belongs to the technical field of fermentation engineering.

BACKGROUND

Soy sauce originated in China and evolved from sauce. It has a long history and national characteristics. In recent years, the consumer market of soy sauce has expanded from Asia to European and American countries. Because of its delicious taste and mellow mouthfeel, the soy sauce is very popular with people of various countries. Soy sauce is prepared by hydrolyzing and catalyzing raw materials (soybean and wheat) rich in protein and starch into various small molecular substances under the action of a complex enzymatic system produced by filamentous fungi (*Aspergillus sojae* or *Aspergillus oryzae*), and then fermentation by various microorganisms in soy sauce mash.

High-salt dilute-state soy sauce is famous for its rich ester aroma and mellow aroma, but its salt content of 16 g-18 g·100 mL$^{-1}$ is not in line with the development trend of low-salt healthy diet. Excessive consumption of salt is a global health problem and is widely regarded as the cause of cardiovascular disease, stroke and kidney disease (Rhee, M. Y. Sodium intake reduction in real world, *Korean Circ. J.* 2020, 50 (5), 441-442.). Today, the Chinese people consume an average of 10.5 grams of salt per day, while the average consumption level in Europe is 7-13 grams per capita, which are both higher than the 5 grams recommended by the World Health Organization (2012). Therefore, the "China's Industrial Salt Reduction Plan" recommends that per capita salt intake be reduced by 20% by 2030 (Chinese Nutrition Society, 2018). At present, the salt reduction rate of low-salt soy sauce produced by a high-salt dilute -state process in China is 25%-30%, and some can reach 45%. The salt content in soy sauce is less than or equal to 12 g·100 mL$^{-1}$, and ultra-low levels of less than or equal to 9 g·100 mL$^{-1}$ are rare. On the whole, products with added preservatives, containing salt reduced by 25%-30%, and with a marked salt content of less than or equal to 12 g·100 mL$^{-1}$ belong to low-salt soy sauce. Soy sauce products without preservatives, containing salt reduced by 40% or more, or with a marked salt content of less than or equal to 9 g·100 mL$^{-1}$ are the lowest-level products. Although soy sauce can be produced by a low-salt solid-state fermentation process, there are significant differences in the flavor composition, physicochemical properties, cooking requirements and the like between the soy sauce fermented by the low-salt solid-state fermentation and the high-salt dilute-state fermented soy sauce, which are two different types of soy sauce. Therefore, the soy sauce produced by the low-salt solid-state method cannot replace the high-salt dilute-state fermented soy sauce, and the high-salt dilute-state soy sauce cannot be fermented by the low-salt solid-state soy sauce fermentation by reducing water activity and carrying out high-temperature fermentation to achieve salt-reduced fermentation. Therefore, high-salt dilute-state soy sauce with a low salt content is often by desalting after fermentation, adjusting the degree of fermentation, lowering the fermentation temperature or increasing the sterility of the environment, and it is necessary to add preservatives to ensure the quality stability in the product shelf life. Whether desalting or the degree of fermentation is adjusted and the fermentation conditions are controlled, it will significantly increase the production cost, and may also reduce the flavor, quality and safety of the product. Therefore, the use of beneficial microorganisms to synergize salt-reduced fermentation of soy sauce is of great significance to promote the development and application of low-salt fermentation technology for high-salt dilute-state soy sauce such and realize mass production and promotion of low-salt high- salt dilute-state soy sauce.

SUMMARY

The objective of the present disclosure is to overcome the deficiencies in the prior art and provide a low-salt soy sauce fermentation technology, which, by changing a microbial fermentation process of high-salt dilute-state soy sauce, can ensure normal progress of low-salt fermentation of soy sauce without changing the flavor and quality of the soy sauce, reduce the number of miscellaneous bacteria and spoilage bacteria in the soy sauce, reduce the biogenic amine content in the soy sauce and improve the quality stability in the shelf life of the soy sauce.

The present disclosure provides *Weissella paramesenteroides* JL-5, preserved in the China Center for Type Culture Collection on Jun. 9, 2021, with a preservation number of CCTCC NO: M 2021707.

The present disclosure further provides a method for culturing the *W. paramesenteroides* JL-5, in which the *W. paramesenteroides* JL-5 is cultured in a medium containing a carbon source, a nitrogen source and inorganic salts at a suitable temperature.

In an embodiment, the method includes inoculating the *W. paramesenteroides* JL-5 into an MRS medium, and performing static culture at 30-40° C., or 35-37° C., or 37° C.

The present disclosure further provides *Bacillus amyloliquefaciens* JDF-2, preserved in the China Center for Type Culture Collection on Jun. 21, 2021, with a preservation number of CCTCC NO: M 2021737.

The present disclosure further provides a starter containing the *W. paramesenteroides* JL-5 and/or the *B. amyloliquefaciens* JDF-2, wheat koji, bran koji or other types of koji for fermentation.

The present disclosure further provides a method for producing high-salt dilute-state soy sauce, including steaming, koji making, and fermentation.

The fermentation includes: mixing finished koji with brine at a volume ratio of 1:(2-3), so that the final concentration of salt in the system is less than or equal to 12 g·100 mL$^{-1}$, adding *W. paramesenteroides* JL-5 and *B. amyloliquefaciens* JDF-2, or a composition containing the *W. paramesenteroides* JL-5 and the *B. amyloliquefaciens* JDF-2, and then performing fermentation at 25-30° C. for at least 30 days.

The *W. paramesenteroides* JL-5 was preserved in the China Center for Type Culture Collection on Jun. 9, 2021, with a preservation number of CCTCC NO: M 2021707.

The *B. amyloliquefaciens* JDF-2 was preserved in the China Center for Type Culture Collection on Jun. 21, 2021, with a preservation number of CCTCC NO: M 2021737.

In an embodiment, the concentration of the *W. paramesenteroides* JL-5 is greater than or equal to $1.0\times10^7$ CFU·g$^{-1}$, and the concentration of the *B. amyloliquefaciens* JDF-2 is greater than or equal to $1.0\times10^6$ CFU·g$^{-1}$.

In an embodiment, the finished koji is prepared by the following method: uniformly mixing defatted soybeans with water to obtain a mixture, uniformly mixing the mixture with wheat flour at a mass ratio of (4-6):1, adding a soy sauce koji starter accounting for 1-1.5% of the total mass of the mixed raw materials, performing uniform mixing, and then performing culturing at 28° C.-30° C., wherein the koji is turned at the right time, and the koji making process takes 40 h-48 h.

In an embodiment, the composition is a starter containing the *W. paramesenteroides* JL-5 and the *B. amyloliquefaciens* JDF-2, wheat koji, bran koji or other types of koji for fermentation.

In an embodiment, the method includes the following steps:

(1) koji making process: Defat soybeans were steamed at 121° C. (0.1 MPa) for 20 min., uniformly mixing the cooled soybean with wheat flour at a mass ratio of (4-6):1, adding a soy sauce koji starter accounting for 1-1.5% of the total mass of the mixed raw materials, and then performing culturing at 28° C.-30° C., wherein the koji is turned at the right time, and the koji making process takes 40 h-48 h; and (2) fermentation process: mixing the finished koji prepared in step (1) with brine containing NaCl at a volume ratio of 1:(2-3), so that the final concentration of salt in the system is less than or equal to 12 g·100 mL$^{-1}$, adding the *W. paramesenteroides* JL-5 and/or the *B. amyloliquefaciens* JDF-2, or adding the starter, wheat koji, bran koji or other types of koji for fermentation, and performing fermentation at 25° C.-30° C. for 40 days; after fermentation to day 3 to day 5, adding *Zygosaccharomyces rouxii* ZQ01, and performing stirring at the right time during the fermentation.

In an embodiment, the method makes the prepared soy sauce have at least one of the following features (a)-(e):

(a) the number of spoilage bacteria in the soy sauce moromi mash is reduced;

(b) the salt content in the soy sauce is less than or equal to 12 g·100 mL$^{-1}$;

(c) the biogenic amine content in the soy sauce is reduced;

(d) the quality stability in the shelf life of soy sauce is improved; and (e) the formation of volatiles in soy sauce is promoted.

In an embodiment, the soy sauce includes, but is not limited to, soy sauce without added preservatives.

In an embodiment, the spoilage bacteria include, but are not limited to, at least one of: *Bacillus subtilis*, *Bacillus halodurans*, *Bacillus megaterium*, *Staphylococcus saprophytics*, *Kurthia zopfii*, *Kurthia gibsonii*, and *Lactobacillus pobuzihii*.

The present disclosure further provides a salt-reduced fermentation method for high-salt dilute-state soy sauce, including mixing the prepared finished koji with brine at a volume ratio of 1:(2-3), so that the final concentration of salt in the system is less than or equal to 12 g·100 mL$^{-1}$, and then performing fermentation at 25-30° C. for at least 30 days, wherein stirring is performed every day during the fermentation.

In an embodiment, the method includes: mixing the prepared finished koji with brine at a volume ratio of 1:(2-3), so that the final concentration of salt in the system is 9-12 g·100 mL$^{-1}$, and then performing fermentation at 25-30° C. for 30 days, wherein stirring is performed at right times during the fermentation.

In an embodiment, the method is specifically: mixing the prepared finished koji with brine containing 200 g·L$^{-1}$ NaCl at a volume ratio of 1:(2-3) to make the final concentration of salt in the soy sauce mash system reach 12 g·100 mL$^{-1}$, adding 10$^7$ CFU·g$^{-1}$ *Z. rouxii* ZQ01 on day 3-5 of fermentation, and fermenting the mixture at 30° C. for 40 days while performing stirred once a day during the fermentation.

The present disclosure further provides application of the method in the production of high-salt dilute-state soy sauce.

In an embodiment, the production of the high-salt dilute-state soy sauce includes a koji making process and a fermentation process.

In an embodiment, the koji making process includes: uniformly mixing defatted soybeans with wheat flour at a ratio of (4-6): 1, then adding a soy sauce koji starter amounting of 1.5% of the total mass of the materials (after the defatted soybeans and the wheat flour are mixed), and performing culturing at 30° C. for 48 h, wherein the koji is turned at the right time, and the finished koji is prepared when the surface of the koji is covered with yellow-green hyphae.

In an embodiment, the production of the high-salt dilute-state soy sauce includes the following steps:

(1) koji making: Defat soybeans were steamed at 121° C. (0.1 MPa) for 20 min., uniformly mixing the cooled soybean with wheat flour at a mass ratio of (4-6):1, then adding a soy sauce koji starter accounting for 1.5% of the total weight of the mixed defatted soybeans and wheat flour, uniformly mixing the mixed materials, and performing culturing at 30° C., wherein the koji is turned at the right time, the koji making process takes 48 h, and the finished koji is prepared when the surface of the koji is covered with yellow-green hyphae; and (2) fermentation: mixing the prepared finished koji with brine containing 200 g·L$^{-1}$ NaCl at a volume ratio of 1:(2-3), so that the final concentration of salt in the mixed soy sauce mash system reaches 12 g·100 mL$^{-1}$, adding 10$^7$ CFU·g$^{-1}$ *Z. rouxii* ZQ01 on day 3-5 of fermentation, and fermenting the mixture at 30° C. for 40 days while stirring the mixture once a day during the fermentation.

In an embodiment, in step (2), the *W. paramesenteroides* JL-5 and/or the *B. amyloliquefaciens* JDF-2 was inoculated; and the final concentration of the *W. paramesenteroides* JL-5 and the *B. amyloliquefaciens* JDF-2 in the fermentation system is $1.0\times10^6$-$1.0\times10^8$ CFU·g$^{-1}$.

In an embodiment, the concentration of the *W. paramesenteroides* JL-5 in a soy sauce mash environment containing salt with a concentration of 12 g·100 mL$^{-1}$ is at least $1.0\times10^7$ CFU·g$^{-1}$.

In an embodiment, the *W. paramesenteroides* JL-5 or the starter containing the *W. paramesenteroides* JL-5 and the *B. amyloliquefaciens* JDF-2 are added simultaneously.

In an embodiment, the ratio of the number of bacterial cells of the *W. paramesenteroides* JL-5 to that of the *B. amyloliquefaciens* JDF-2 is 1:1.

The present disclosure further provides crude soy sauce obtained by fermentation with the method, wherein the salt content is less than or equal to 12 g·100 mL$^{-1}$, the sodium content is 380-420 mg·10 mL$^{-1}$, and the amino acid nitrogen content is greater than or equal to 1.2 g·100 mL$^{-1}$.

In an embodiment, the crude soy sauce obtained by the fermentation has a salt content of 9.8 g·100 mL$^{-1}$, a sodium content of 412 mg·10 mL$^{-1}$, and an amino acid nitrogen content greater than or equal to 1.2 g·100 mL$^{-1}$.

The present disclosure further provides a method for improving the shelf-life stability of low-salt soy sauce without adding preservative, in which *B. amyloliquefaciens* and *W. paramesenteroides* are added for synergistic fermentation before the low-salt soy sauce is fermented, and in the low-salt soy sauce fermentation system, the concentration of the *B. amyloliquefaciens* is at least $1.0 \times 10^6$-$1.0 \times 10^8$ $CFU \cdot g^{-1}$, and the concentration of the *W. paramesenteroides* is at least $1.0 \times 10^7$ $CFU \cdot g^{-1}$.

Beneficial Effects

1. By separating and purifying microorganisms in soy sauce mash, the present disclosure obtains *W. paramesenteroides* JL-5 which can significantly inhibit miscellaneous bacteria or spoilage bacteria such as *B. megaterium*, *B. halodurans*, *B. subtilis*, and *S. saprophytics* during the fermentation of low-salt soy sauce, and *B. amyloliquefaciens* JDF-2 which can significantly inhibit the growth of spoilage bacteria such as *K. zopfii*, *K. gibsonii*, and *L. pobuzihii* during the fermentation of low-salt soy sauce. The strains obtained by screening by the present disclosure can be used alone or together to prepare a seasoning starter or koji for fermented food.

2. The present disclosure uses the *W. paramesenteroides* JL-5 alone or together with the *B. amyloliquefaciens* JDF-2 for soy sauce fermentation, thereby well inhibiting the growth of miscellaneous bacteria and spoilage bacteria in the low-salt soy sauce fermentation system with a salt concentration of $12$ $g \cdot 100$ $mL^{-1}$. Compared with $18$ $g \cdot 100$ $mL^{-1}$ high-salt dilute-state soy sauce, the content of esters can be significantly increased in thevolatiles of the fermented low-salt soy sauce.

3. The present disclosure develops a new microbial fermentation process for high-salt dilute-state soy sauce by adjusting the addition amount and method of the *W. paramesenteroides* JL-5, and without reducing the content of volatiles in the low-salt fermented soy sauce obtained by fermentation, the biogenic amine content, the number of spoilage bacteria and miscellaneous bacteria, and the salt content are all significantly reduced.

4. The microbial fermentation process of high-salt dilute-state soy sauce provided by the present disclosure can make the obtained soy sauce have a salt content as low as $9.8$ $g \cdot 100$ $mL^{-1}$, a sodium content of $412$ $mg \cdot 10$ $mL^{-1}$, and an amino acid nitrogen content of greater than or equal to $1.2$ $g \cdot 100$ $mL^{-1}$, the total number of microorganisms in the soy sauce stored for 60 days without adding any preservatives is not significantly different from that of traditional high-salt dilute-state soy sauce, and the obtained soy sauce meets the Chinese Hygienic Standard for Soy Sauce GB2717-2018 and the Japanese Quality Standard for Soy Sauce G/TBT/N/JPN/297, and has good quality stability in the shelf life.

Biomaterial Preservation

*W. paramesenteroides*, classified as *W. paramesenteroides* JL-5, has been preserved in the China Center for Type Culture Collection on Jun. 9, 2021, with a preservation number of CCTCC NO: M 2021707, and the preservation address is the China Center for Type Culture Collection, Wuhan University, Wuhan, China.

*B. amyloliquefaciens*, classified as *B. amyloliquefaciens* JDF-2, has been preserved in the China Center for Type Culture Collection on Jun. 21, 2021, with a preservation number of CCTCC NO: M 2021737, and the preservation address is the China Center for Type Culture Collection, Wuhan University, Wuhan, China.

DETAILED DESCRIPTION

Strains and Materials

Figure 1A:
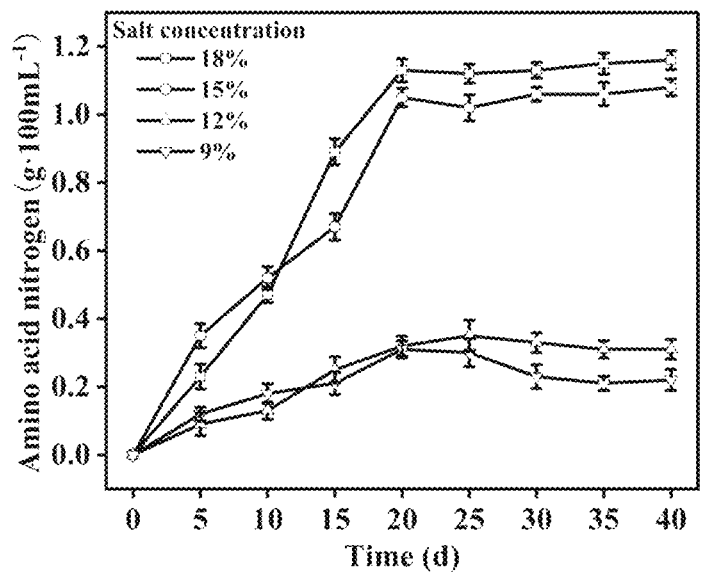
FIG. 1A shows the changes in the amino acid nitrogen content of soy sauce mash in fermentation processes with different salt concentrations.
Figure 1B:
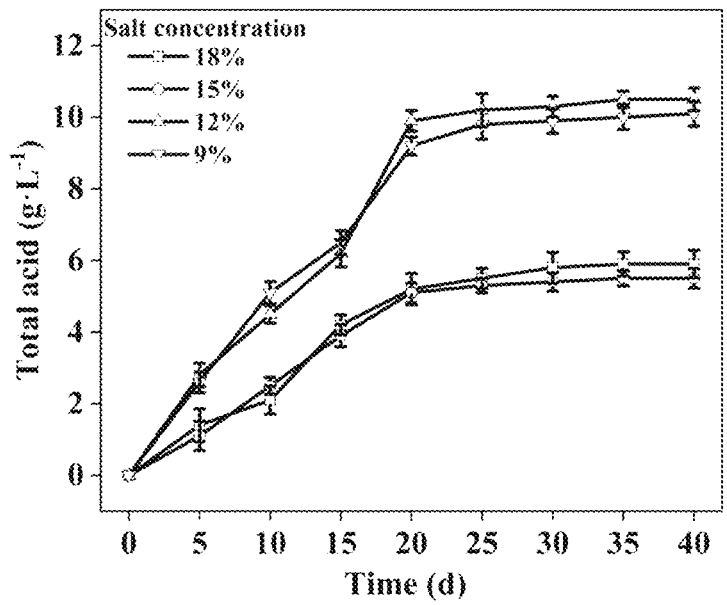
FIG. 1B shows the changes in the total acid content of the soy sauce mash in fermentation processes with different salt concentrations.

Z. rouxii ZQ01: Disclosed in "Study on the Production Mechanism and Elimination Strategies of Ethyl Carbamate in Soy Sauce", the applicant promised to release the biological material to the public within 20 years from the filing date.

Soy sauce koji starter: A soy sauce koji starter is prepared by drying and separating to extract effective spores from Aspergillus oryzae and Aspergillus niger with high protease activity and glucoamylase activity, and the spore content is greater than or equal to $10,000 \cdot g^{-1}$.

Media

MRS medium: 10 $g \cdot L^{-1}$ peptone, 8 $g \cdot L^{-1}$ beef extract powder, 4 $g \cdot L^{-1}$ yeast extract powder, 20 $g \cdot L^{-1}$ glucose, 2 $g \cdot L^{-1}$ dipotassium hydrogen phosphate, 2 $g \cdot L^{-1}$ diammonium hydrogen citrate, 5 $g \cdot L^{-1}$ sodium acetate, 0.2 $g \cdot L^{-1}$ magnesium sulfate, 0.04 $g \cdot L^{-1}$ manganese sulfate, and 1 $gL^{-1}$ Tween 80.

Rose bengal medium: 5 $g \cdot L^{-1}$ peptone, 10 $g \cdot L^{-1}$ glucose, 1 $g \cdot L^{-1}$ dipotassium hydrogen phosphate, 0.5 $g \cdot L^{-1}$ magnesium sulfate, 20 $g \cdot L^{-1}$ agar, and 100 $mL \cdot L^{-1}$ 1/3000 rose bengal solution.

YPD medium: 10 $g \cdot L^{-1}$ yeast extract, 20 $g \cdot L^{-1}$ peptone, and 20 $g \cdot L^{-1}$ glucose.

LB medium: 5 $g \cdot L^{-1}$ yeast extract, 10 $g \cdot L^{-1}$ peptone, and 10 $g \cdot L^{-1}$ sodium chloride.

Soy sauce mash fermentation medium: Raw materials for producing soy sauce, namely defat soybean and wheat flour are mixed at a ratio of 1:1, 4 times of water (w/v) and thermostable amylase (50 $U \cdot kg^{-1}$) are added for cooking and gelatinizing for 1 h, glucoamylase (120 $U \cdot kg^{-1}$) is added for saccharifying at 60° C. for 2 h, and sterilizing is carried out at 121° C. for 20 min to obtain a simulated fermentation medium.

Detection Methods

The total acid concentration is measured by a sodium hydroxide titration method. The pH of a soy sauce mash sample is measured using a pH meter. The amino acid nitrogen concentration is measured by a formol titration method (for the determination method, refer to the method in the reference "Effect of Tetragenococcus halophilus on Soy Sauce Quality Prepared by Fermentation"). The reducing sugar content is determined by the 3,5-dinitrosalicylic acid method (DNS). The salt content is determined using a silver nitrate titration method (refer to "GB 5009.44-2016 National Food Safety Standard Determination of Chloride in Food"), and the sodium content is determined by an atomic absorption method (refer to "GB 5009.91-2017 National Food Safety Standard Determination of Potassium and Sodium in Food").

Detection of biogenic amine content:

(1) Preparation of biogenic amine (mixed standard) standard solutions: 1 mL is pipetted from each of 8 kinds of biogenic amine solutions (with a mass concentration of 1,000 $mg \cdot L^{-1}$): putrescine, cadaverine, spermine, spermidine, tryptamine, histamine, tyramine and phenethylamine, and added to a 10 mL volumetric flask, the solutions are diluted to a volume of 10 mL with a 0.1 $mol \cdot L^{-1}$ hydrochloric acid solution, the mixtures are uniformly mixed, and a biogenic amine standard (100 $mg \cdot L^{-1}$) is prepared. Biogenic amine standard series solution: The biogenic amine standard mixed solution is diluted with 0.1 $mol \cdot L^{-1}$ hydrochloric acid into biogenic amine standard series solutions with a mass concentration of 5 $mg \cdot L^{-1}$, 10.0 $mg \cdot L^{-1}$, 25.0 $mg \cdot L^{-1}$, 50.0 $mg \cdot L^{-1}$ and 100.0 $mg \cdot L^{-1}$, and the solutions are prepared just before use. Standard solutions as internal standards: An appropriate amount of 1,7-diaminoheptane is weighed and prepared with a 0.1 $mol \cdot L^{-1}$ HCl solution to a mass concentration of 100 $mg \cdot L^{-1}$. Dansyl chloride derivatizing agent: An appropriate amount of dansyl chloride is weighed and dissolved with acetone. The prepared solution has a mass concentration of 10 $mg \cdot mL^{-1}$, and is prepared just before use.

(2) Sample pretreatment: 10 mL of a soy sauce sample is accurately measured and put in a 50 mL centrifuge tube, 20 mL of a 5% (w/v) trichloroacetic acid solution is added and uniformly mixed, vibrating extraction is performed for 60 min, the extract is centrifuged at 8,000 $r \cdot min^{-1}$ for 10 min to take the supernatant, extraction is performed twice, and the supernatants are combined, diluted to 25 mL and filtered with filter paper. 2 mL of the soy sauce sample extract is accurately pipetted into a 15 mL centrifuge tube, 3 mL of n-hexane is added, and the mixture is shaken for 2 min, allowed to stand for layering, and centrifuged at 8,000 $r \cdot min^{-1}$ for 10 min to obtain the supernatant.

(3) Sample derivatization: 500 µL of the sample pretreatment solution and the biogenic amine standard series solutions are pipetted respectively, 50 µL of internal standard (100 $mg \cdot L^{-1}$), 100 µL of a NaOH solution (2 $mol \cdot L^{-1}$) and 150 µL of a saturated $NaHCO_3$ buffer are added respectively, and then 75 µL of a dansyl chloride derivatizing solution is added. The mixture is placed in a 45° C. water bath after uniform mixing to react in the dark for 50 min, and then 50 µL of ammonia is added to stop the reaction. After standing in the dark for 30 min, the volume is adjusted to 2.5 mL with acetonitrile, the mixture is centrifuged at 8,000 $r \cdot min^{-1}$ for 10 min, and the supernatant is filtered with a 0.22 µm pore filter membrane for determination.

(4) Quantitative determination of biogenic amine adopts high performance liquid chromatography (HPLC), wherein the mobile phase A is acetonitrile, the mobile phase B is ultrapure water, the column temperature is 30° C., the flow rate is 0.8 $mL \cdot min^{-1}$, the injection volume is 10 µL, and the UV detection wavelength is 254 nm. In an elution procedure, within 0-7 min, the mobile phase A is kept at 55%; within 7-14 min, the mobile phase A is kept at 65%, and then kept at 70% for 6 min; and the mobile phase A is restored from 70% to 55% within the last 1 min.

Volatiles are determined by solid-phase micro-extraction combined with gas chromatography-mass spectrometry (SPME-GC-MS), and for the specific method, refer to patent application CN112852667A "Effect of Enrichment of Tetragenococcus Halophilus on Simulated Fermentation of Low-Salt Soy Sauce" published in 2021.

Example 1

Preparation of High-Salt Dilute-State Soy Sauce Fermentation with Reduced Salt Content (1) Koji making:
The raw materials for koji making include defatted soybeans and wheat flour at a mass ratio of 6:4.

The specific steps are as follows: Defat soybeans were steamed at 121° C. (0.1 MPa) for 20 min., uniformly mixing the cooled soybean with wheat flour at a mass ratio of (4-6):1 and then a soy sauce koji starter accounting for 1.5% of the total mass of the mixed raw materials was added. After uniform mixing, the mixed raw materials were cultured in a biochemical incubator at 28° C.-30° C., the koji was turned at the right time, and the finished koji was prepared after 40 h-48 h when the surface of the koji material was covered with yellow-green hyphae.

(2) Fermentation: The finished koji prepared in step (1) was mixed with brine containing 200 $g \cdot L^{-1}$ NaCl at a volume ratio of 1:(2-3). The uniformly mixed soy sauce mash was put into a 5 L beaker to make the final concentration of salt in the system reach 12 $g \cdot 100$ $mL^{-1}$, then *Z. rouxii* ZQ01 with a final concentration of $10^7$ $CFU \cdot g^{-1}$ was added in day 3-day 5, and the soy sauce mash was fermented at 30° C. for 40 days and stirred once a day during fermentation.

Following the steps (1)-(2), the concentrations of brine added were adjusted respectively, thus the initial salt concentrations of the systems for fermentation were 18 $g \cdot 100$ $mL^{-1}$, 15 $g \cdot 100$ $mL^{-1}$, 12 $g \cdot 100$ $mL^{-1}$ and 9 $g \cdot 100$ $mL^{-1}$ respectively, and samples were taken on day 0, day 5, day 10, day 15, day 20, day 25, day 30, day 35 and day 40 respectively.

Figure 1:
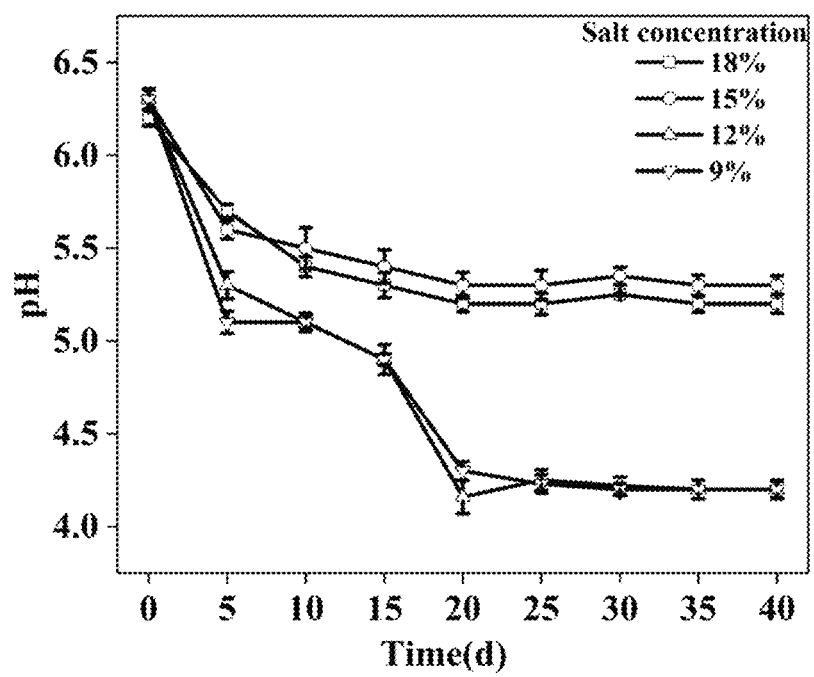
FIG. 1C shows the changes in pH of the soy sauce mash in fermentation processes with different salt concentrations.

(a) Physicochemical indexes in a salt-reduced fermentation process of high-salt dilute -state soy sauce:

5 g of soy sauce mash samples with different salt concentrations were collected, ground and dissolved in 100 mL of normal saline to detect the physicochemical indexes. As shown in FIG. 1, after 40 days of fermentation, the amino acid nitrogen content of the fermented soy sauce mash under the salt concentrations of 12 $g \cdot 100$ $mL^{-1}$ and 9 $g \cdot 100$ $mL^{-1}$ significantly was decreased to 0.31 $g \cdot 100$ $mL^{-1}$ and 0.22 $g \cdot 100$ $mL^{-1}$, which are not in line with the Chinese Hygienic Standard for Soy Sauce GB2717-2018 (0.4 $g \cdot 100$ $mL^{-1}$) and the Japanese Quality Standard for Soy Sauce G/TBT/N/JPN/297. The total acid content was increased significantly to 10.5 $g \cdot L^{-1}$ and 10.1 $g \cdot L^{-1}$, and the pH value was decreased significantly. Under the salt concentrations of 18 $g \cdot 100$ $mL^{-1}$ and 15 $g \cdot 100$ $mL^{-1}$, the amino acid nitrogen contents of the soy sauce after 40 days of fermentation were 1.18 $g \cdot 100$ $mL^{-1}$ and 1.08 $g \cdot 100$ $mL^{-1}$, which are all in line with Chinese Standard for Special Grade Soy Sauce GB2717-2018 (1 $g \cdot 100$ $mL^{-1}$) and Japanese Quality Standard for Soy Sauce G/TBT/N/JPN/297, and the total acid contents were 5.9 $g \cdot L^{-1}$ and 5.5 $g \cdot L^{-1}$.

Figure 2:
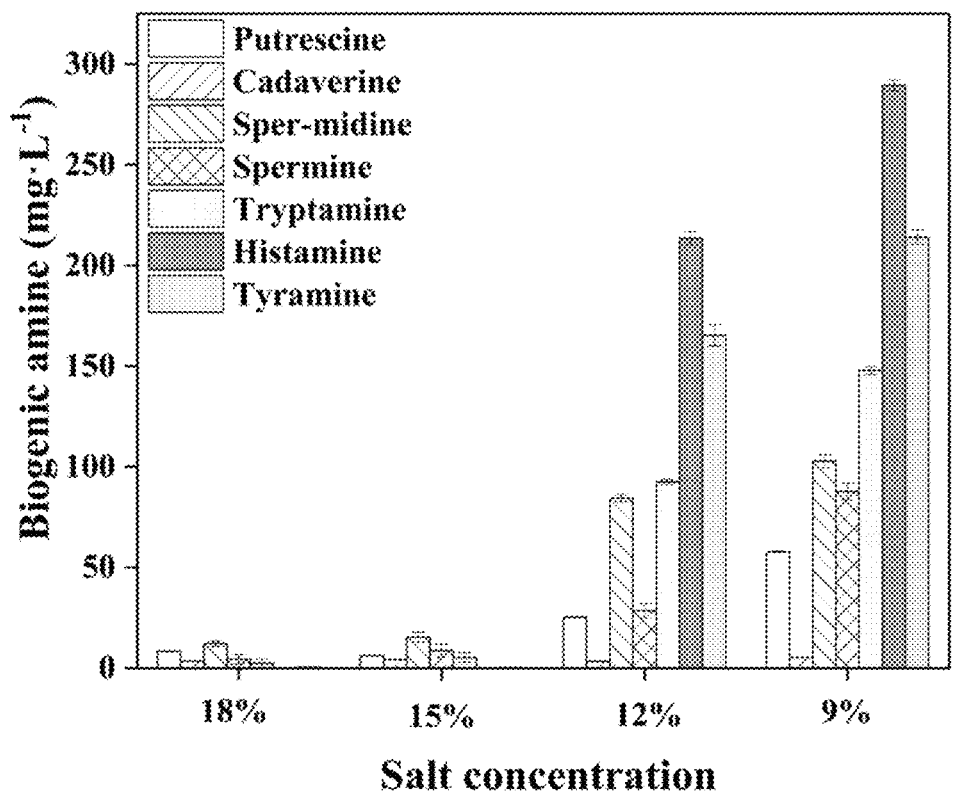
FIG. 2 shows the changes in the biogenic amine content in the soy sauce produced by fermentation with different salt concentrations.

(b) The biogenic amine content of the reduced-salt fermented crude soy sauce of high-salt dilute-state soy sauce:

The biogenic amine contents of soy sauce with different salt concentrations were detected by high performance liquid chromatography. The results are shown in FIG. 2. The contents and types of biogenic amines in soy sauce fermented under salt concentrations of 12 $g \cdot 100$ $mL^{-1}$ and 9 $g \cdot 100$ $mL^{-1}$ were significantly higher than those fermented under salt concentrations of 18 $g \cdot 100$ $mL^{-1}$ and 15 $g \cdot 100$ $mL^{-1}$, and the total biogenic amine contents after 40 days of fermentation were 612.423 $mg \cdot L^{-1}$ and 904.49 $mg \cdot L^{-1}$, respectively. Under the salt concentrations of 18 $g \cdot 100$ $mL^{-1}$ and 15 $g \cdot 100$ $mL^{-1}$, the biogenic amine contents were 18.99 $mg \cdot L^{-1}$ and 39.79 $mg \cdot L^{-1}$.

(c) Volatiles changes of salt-reduced fermented soy sauce:

At the end of fermentation (day 40), three parallel samples were taken from each sample. After filtering and mixing, 5 mL of soy sauce samples were accurately measured and put in 20 mL headspace sample bottles, 83.36 $\mu g \cdot L^{-1}$ 2-octanol was added as an internal standard, the bottles were sealed immediately after mixing, and determination was performed. After the determination, the sample mass spectrum was compared with the NIST 2.0 standard library for identification. volatiles were qualitatively analyzed based on the retention index (RI). According to the area of the internal standard 2-octanol, the volatiles were quantitatively analyzed.

Figure 3:
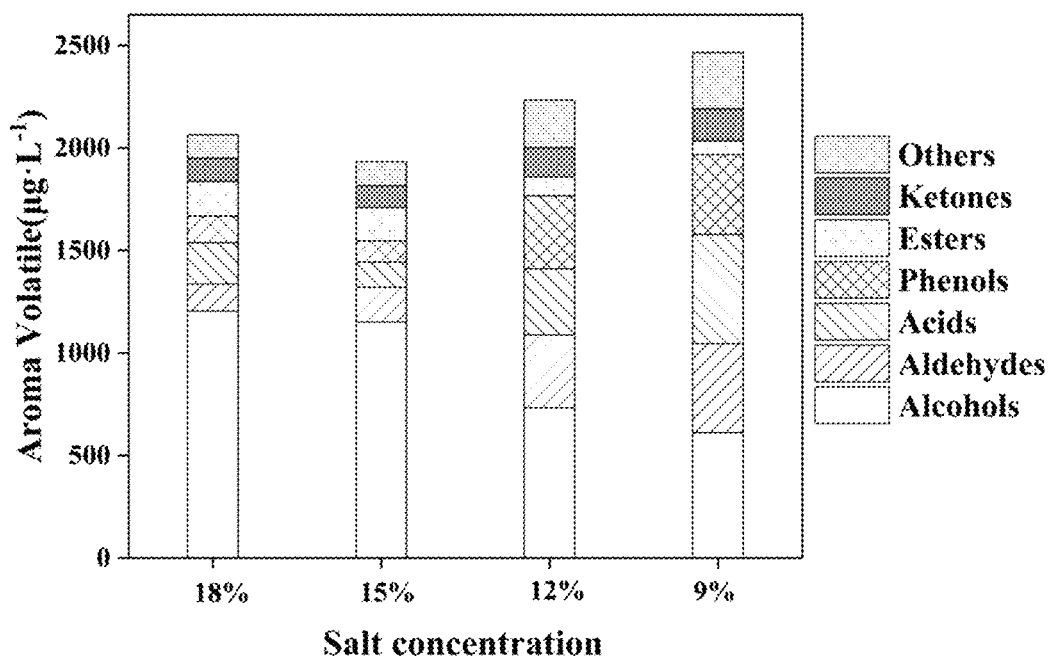
FIG. 3 shows the content and composition of volatiles in the soy sauce produced by fermentation with different salt concentrations.
Figure 4A:
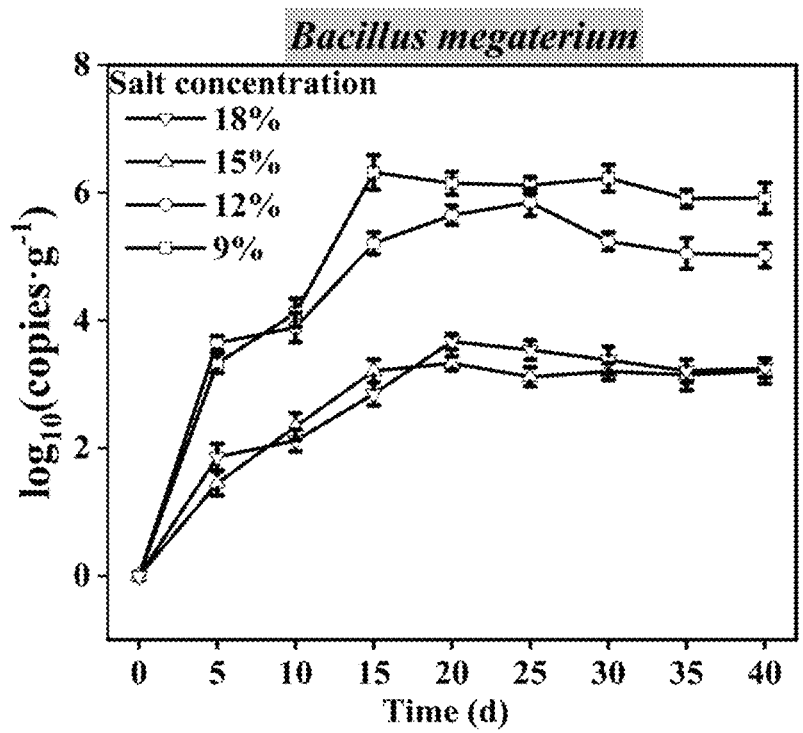
FIG. 4A shows the changes in the number of *B. megaterium* in the soy sauce mash in fermentation processes with different salt concentrations.
Figure 4B:
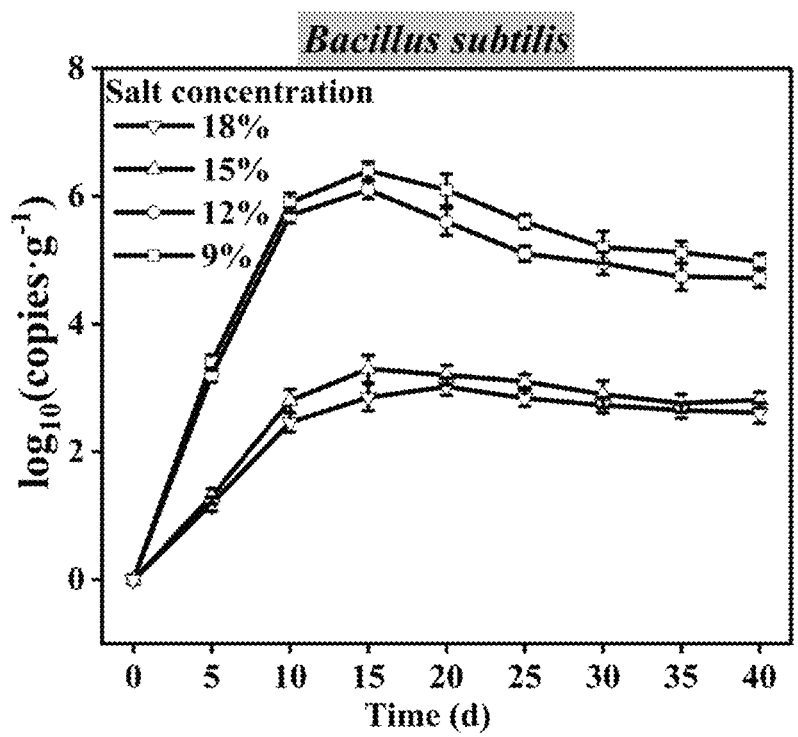
FIG. 4B shows the changes in the number of *B. subtilis* in the soy sauce mash in fermentation processes with different salt concentrations.
Figure 4C:
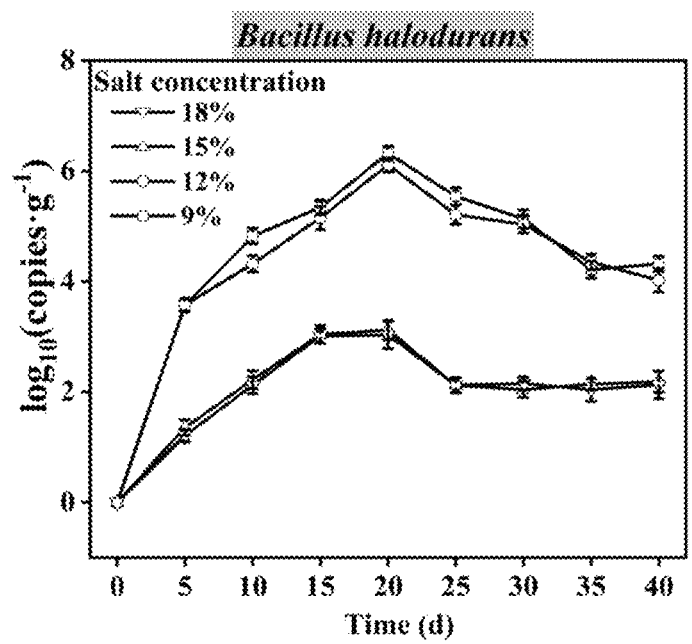
FIG. 4C shows the changes in the number of *B. halodurans* in the soy sauce mash in fermentation processes with different salt concentrations.
Figure 4D:
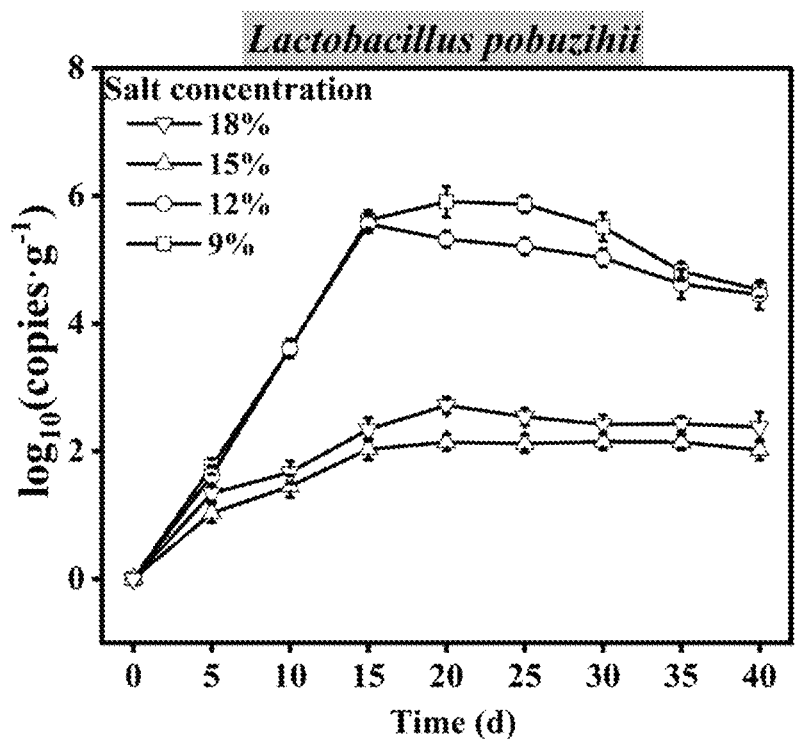
FIG. 4D shows the changes in the number of *L. pobuzihii* in the soy sauce mash in fermentation processes with different salt concentrations.
Figure 4E:
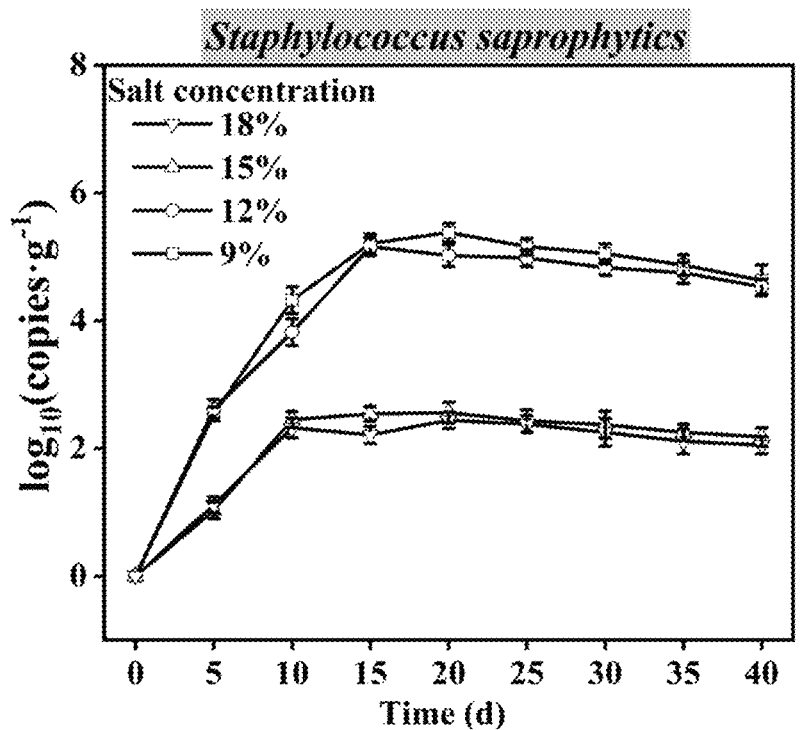
FIG. 4E shows the changes in the number of *S. saprophytics* in the soy sauce mash in fermentation processes with different salt concentrations.
Figure 4F:
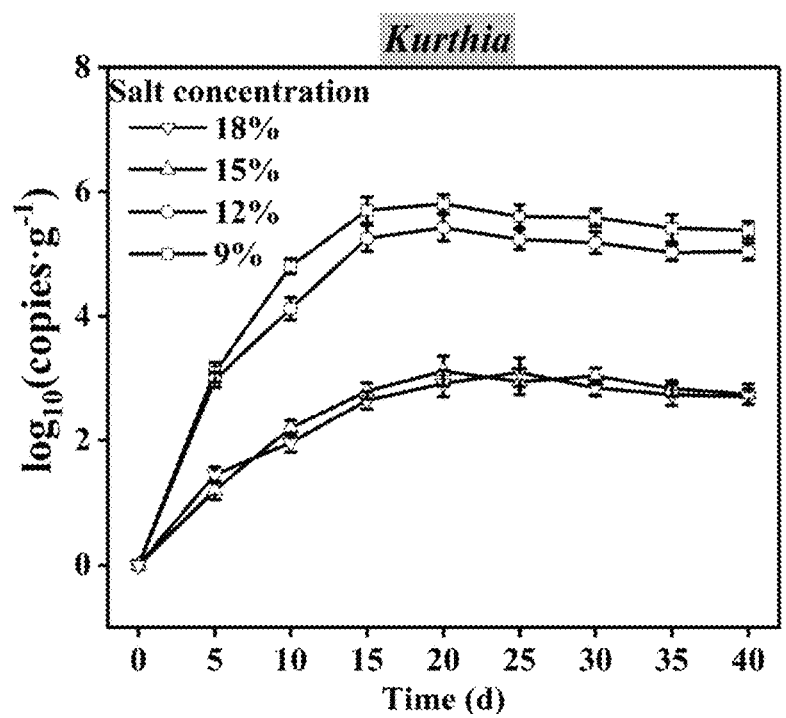
FIG. 4F shows the changes in the number of *Kurthia* in the soy sauce mash in fermentation processes with different salt concentrations.
Figure 5A:
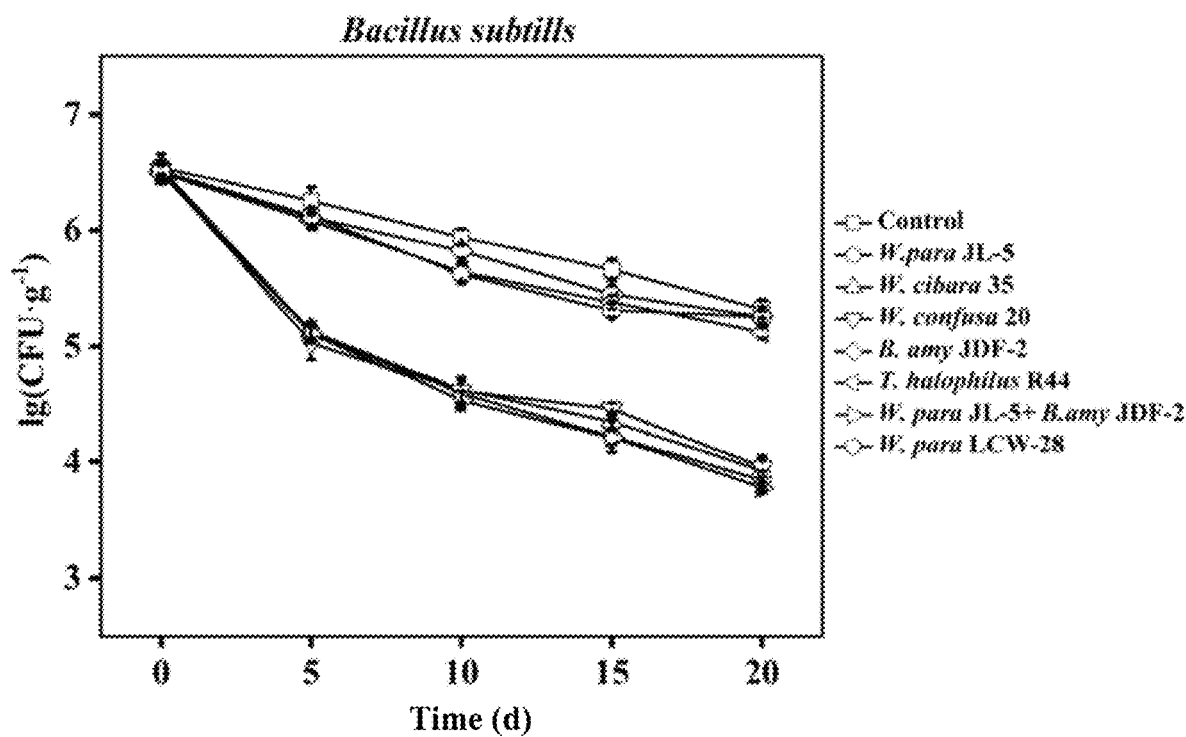
FIG. 5A shows the effects of different fermentation methods on the number of *B. subtilis* in a simulated soy sauce fermentation system.
Figure 5B:
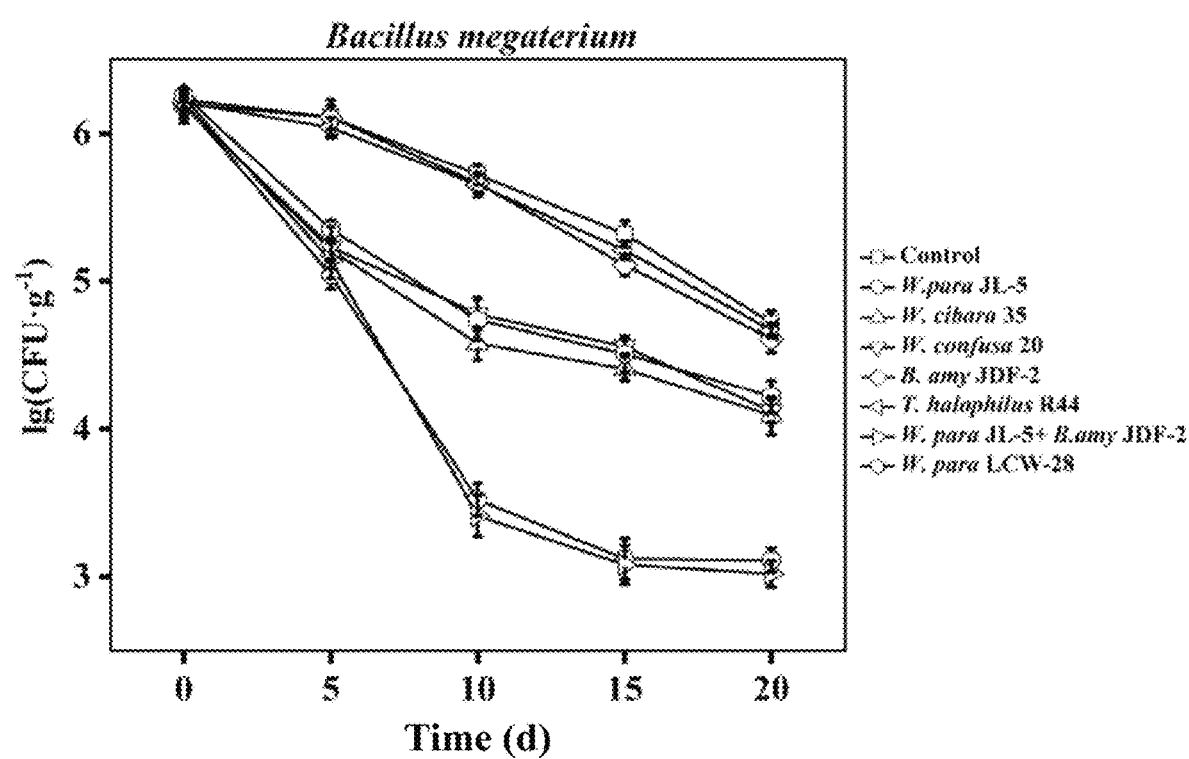
FIG. 5B shows the effects of different fermentation methods on the number of *B. megaterium* in a simulated soy sauce fermentation system.
Figure 5C:
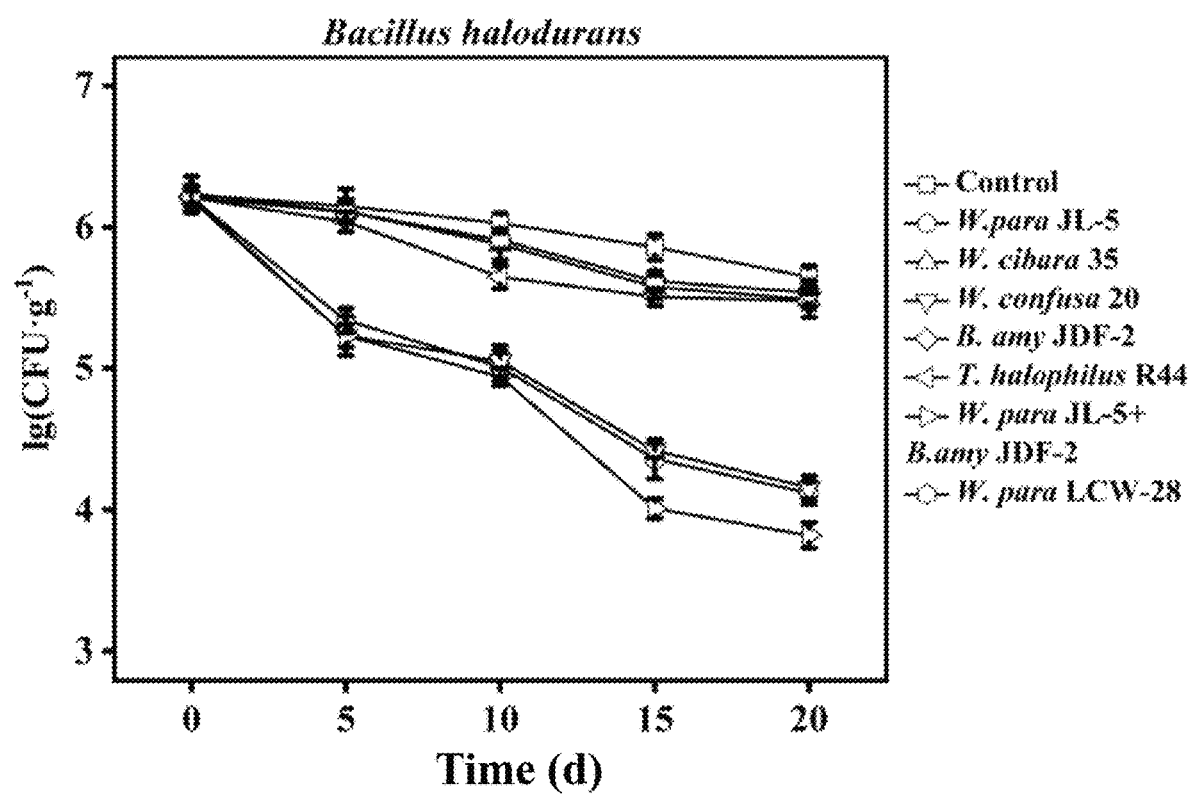
FIG. 5C shows the effects of different fermentation methods on the number of *B. halodurans* in a simulated soy sauce fermentation system.
Figure 5D:
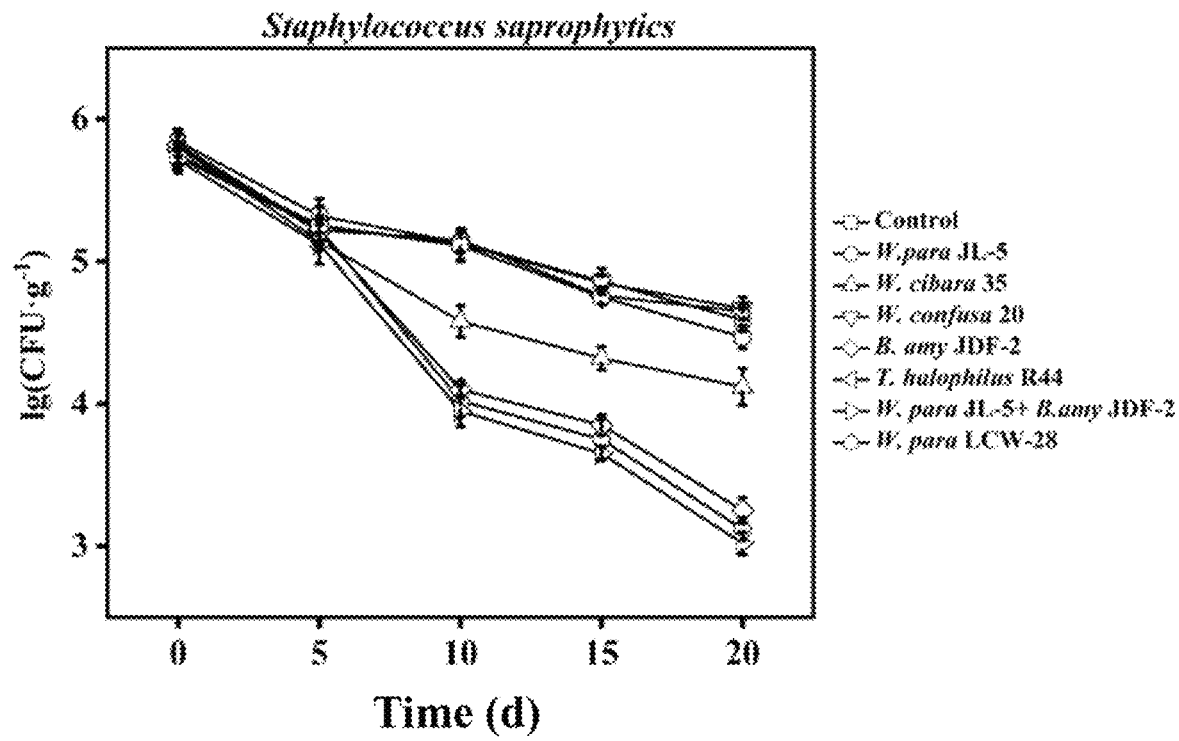
FIG. 5D shows the effects of different fermentation methods on the number of *S. saprophytics* in a simulated soy sauce fermentation system.
Figure 5E:
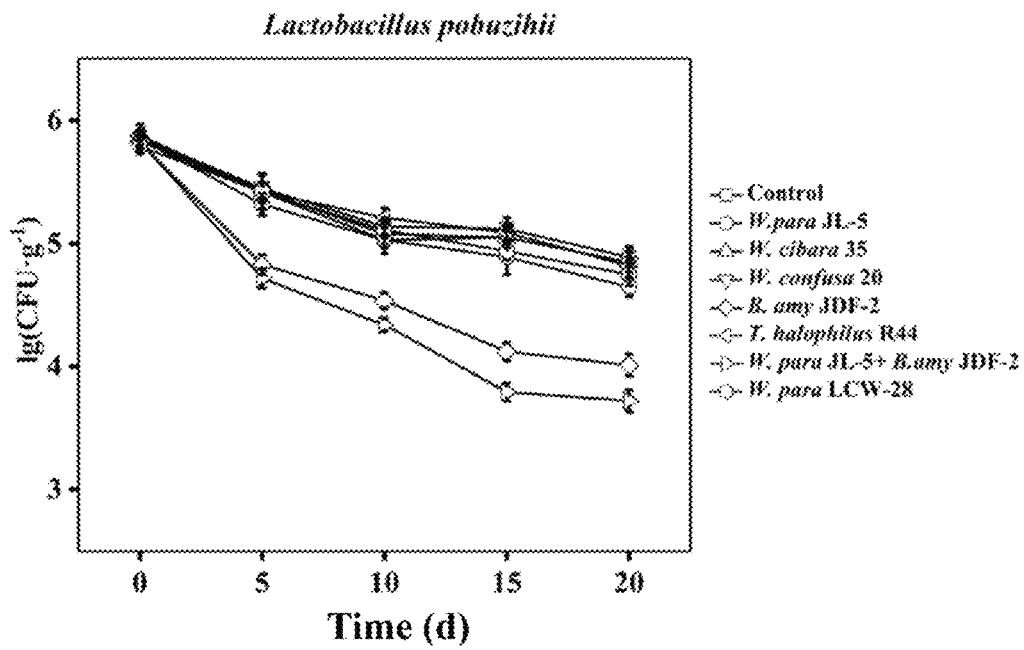
FIG. 5E shows the effects of different fermentation methods on the number of *L. pobuzihii* in a simulated soy sauce fermentation system.
Figure 5F:
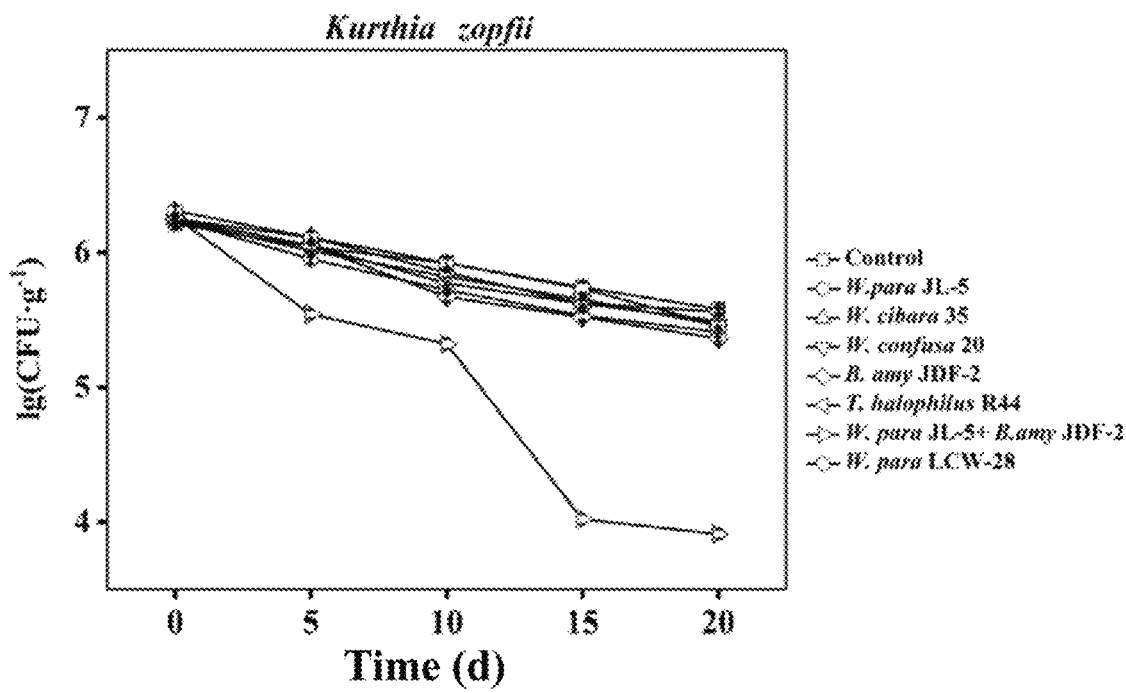
FIG. 5F shows the effects of different fermentation methods on the number of *K. zopfii* in a simulated soy sauce fermentation system.
Figure 6A:
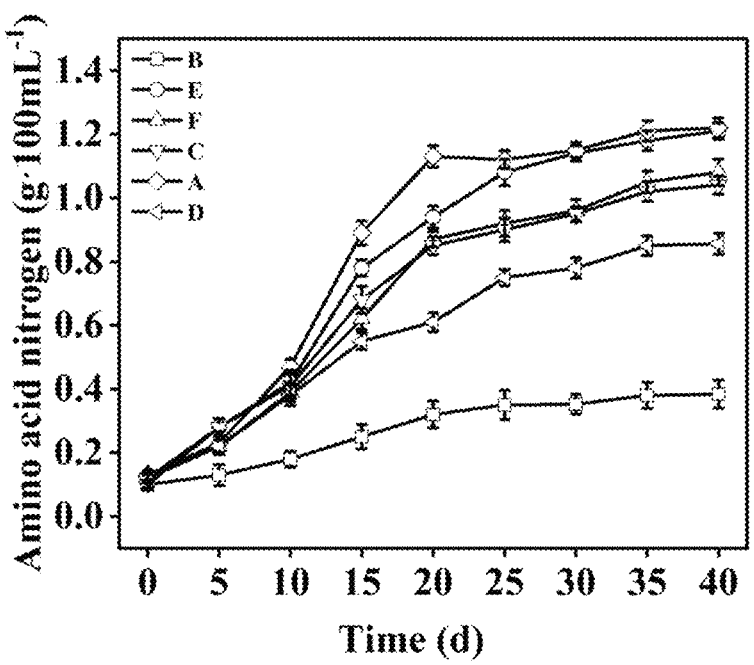
FIG. 6A shows the effects of different fermentation methods on the amino acid nitrogen content of soy sauce.
Figure 6B:
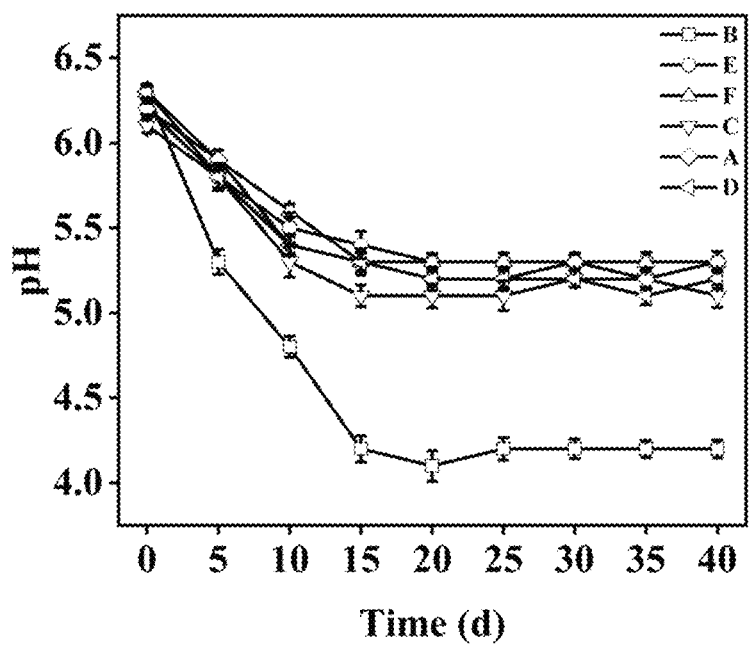
FIG. 6B shows the effects of different fermentation methods on the pH of soy sauce.
Figure 6C:
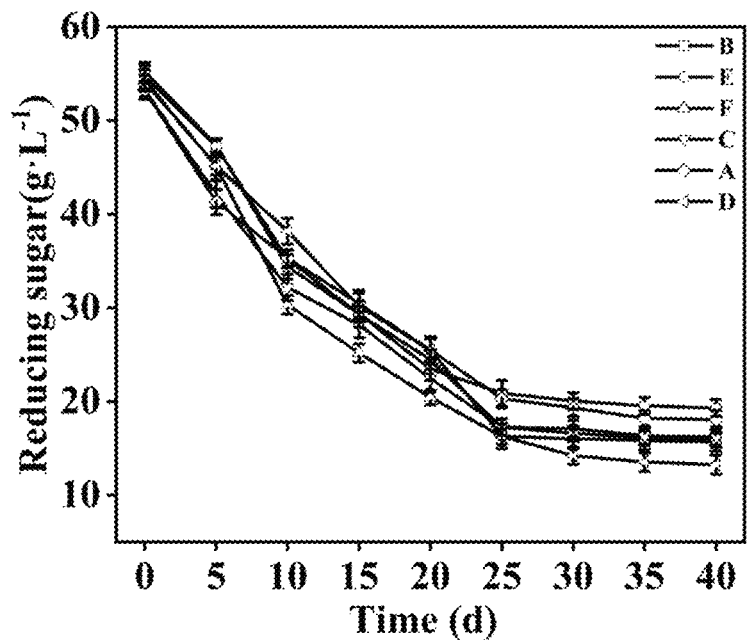
FIG. 6C shows the effects of different fermentation methods on the reducing sugar content of soy sauce.
Figure 6D:
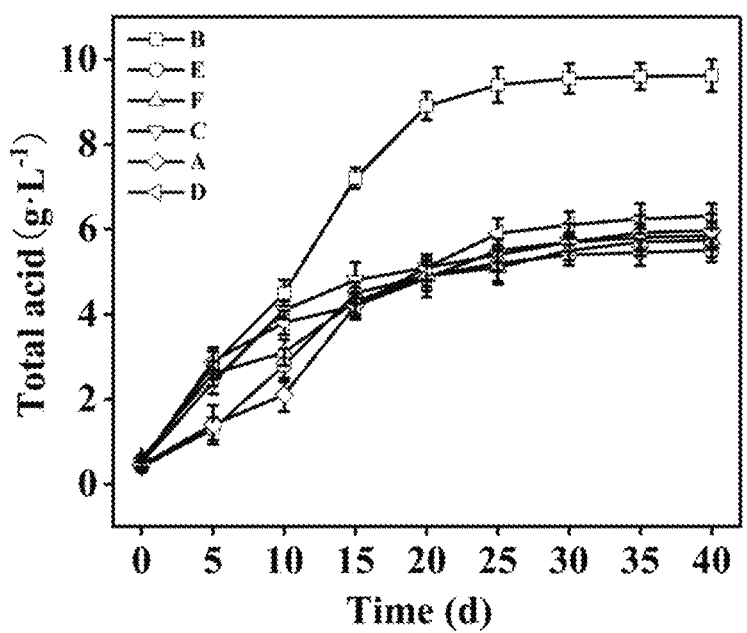
FIG. 6D shows the effects of different fermentation methods on the total acid content of soy sauce.
Figure 7:
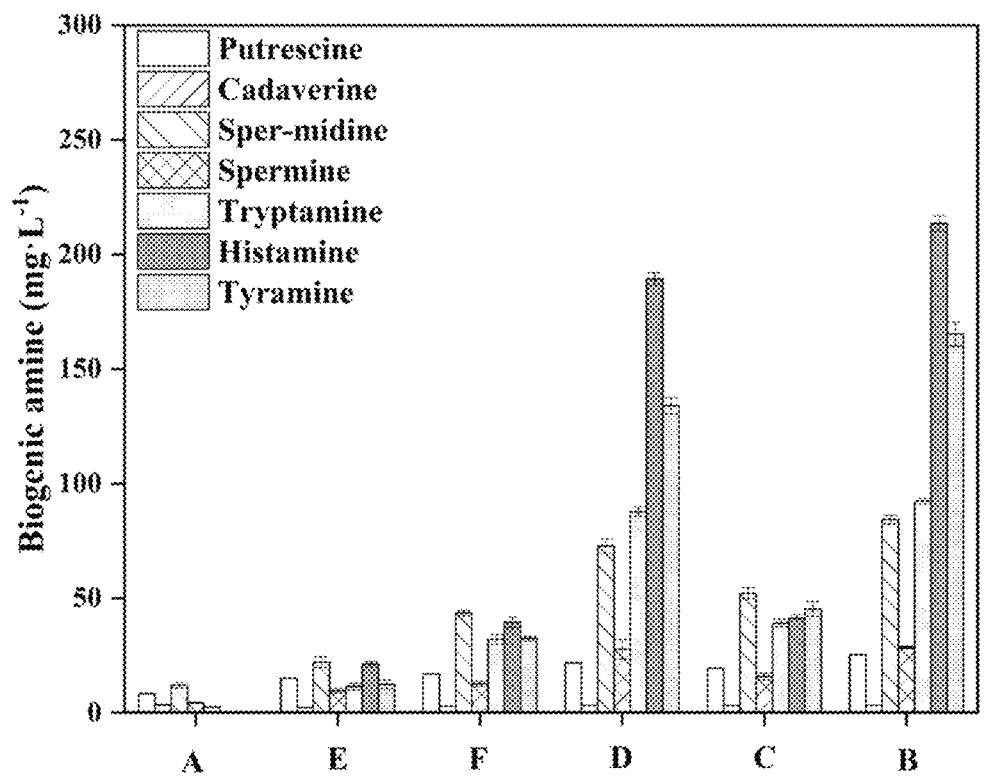
FIG. 7 shows the biogenic amine content of soy sauce produced by different fermentation methods.

The results are shown in FIG. 3. The total volatiles content of the low-salt soy sauce prepared under a salt concentration of 12 $g \cdot 100$ $mL^{-1}$ was increased compared with that in the one prepared in the presence of 18 $g \cdot 100$ $mL^{-1}$ salt. The content of alcohols and esters in the main volatiles of the soy sauce was decreased significantly, the content of 4-ethylguaiacol was decreased by 32.3%; the content of furanone (HEMF) was decreased by 25.4%; the content of 1-octene-3-ol was decreased by 18.4%; the content of alcohols was decreased by 39.2% to 732.15 $\mu g \cdot L^{-1}$; and the content of esters was decreased by 44.59% to 92.33 $\mu g \cdot L^{-1}$.

(d) Changes in spoilage microorganisms in the salt-reduced fermentation process of high-salt dilute-state soy sauce Metagenomic preparation: An appropriate amount of soy sauce mash sample was weighed into a beaker, and washed twice with a sterile saline solution. The washed soy sauce mash was transferred to a mortar, liquid nitrogen was added, and the mixture was ground thoroughly to break cells. Then a microbial genome was extracted by a Power Max® Soil DNA Isolation Kit according to instructions. The concentration of microbial genomic DNA was determined by a Nano Drop2000 ultra-micro spectrophotometer and the purity was evaluated. Specific primers were designed with 16S rDNA sequences of *B. megaterium, B. halodurans, B. subtilis, Kurthia, S. saparophytics,* and *L. pobuzihii* for RT-qPCR amplification. The quantification of microorganisms adopted an absolute quantification method, that is, a standard curve was prepared with a standard substance of known concentration, and the copy number of the sample of unknown concentration was determined. 10-fold gradient dilution was performed on the standard substance, and then the standard substance was used as a template for performing the RT-qPCR reaction. When the reaction was complete, a standard curve was drawn with a cycle threshold Ct as an abscissa and the logarithm of the standard concentration as an ordinate.

TABLE 1

Primers used in this patent

| Target sequences | Primers | Primer sequences (5'-3') | Amplification length (bp) |
|---|---|---|---|
| *Kurthia* | Kur R | CTGGATCACGGTTTACTTCAC (SEQ ID NO: 3) | 182 |
| | Kur F | CCATTACCATCAATACCTGCA (SEQ ID NO: 4) | |

TABLE 1-continued

Primers used in this patent

| Target sequences | Primers | Primer sequences (5'-3') | Amplification length (bp) |
|---|---|---|---|
| L. pobuzihii | Po F | ACTTACTTTCCAAATGTCGA (SEQ ID NO: 5) | 212 |
| | Po R | TCGTTCTAAG TATGGTGCGA (SEQ ID NO: 6) | |
| S. saprophytics | Sta F | CAATTATAAT TAACTAAGGT (SEQ ID NO: 7) | 190 |
| | Sta R | TTACAAGGGA ATCATTAACT (SEQ ID NO: 8) | |
| Bacillus | Bac F | TCATTACAAATATAACAAG (SEQ ID NO: 9) | 167 |
| | Bac R | AGCTTGTTCTACTGTATCC (SEQ ID NO: 10) | |
| B. megaterium | Meg F | TCAGAACTCAGCGAAATCGAGA (SEQ ID NO: 11) | 205 |
| | Meg R | CTATATAAGGAGAGGAATGGT (SEQ ID NO: 12) | |
| B. halodurans | Hal F | TTTGGTGGCGATAGCGAAGAG (SEQ ID NO: 13) | 198 |
| | Hal R | GAGTAGGACGCTGCCAAGC (SEQ ID NO: 14) | |
| B. subtilis | Sub F | ACCGCGTTCGCCTCATTGAACA (SEQ ID NO: 15) | 211 |
| | Sub R | AGCGCTCCAAGCGCTAGCACG (SEQ ID NO: 16) | |

Taking *B. subtilis*, *B. halodurans*, *B. megaterium*, *S. saprophytics*, *K. zopfii* and *L. pobuzihii* as the representative microorganisms of spoilage bacteria, the results are shown in FIG. 4. At the beginning of fermentation, the total number of the spoilage bacteria in the soy sauce fermentation system with different salt concentrations was less than or equal to 50 CFU·$g^{-1}$. In the soy sauce mash sample with a salt concentration of 12 g·100 $mL^{-1}$, the contents of *B. subtilis*, *B. halodurans*, *B. megaterium*, *S. saprophytics*, *K. zopfii* and *L. pobuzihii* at the end of fermentation were $5.3 \times 10^4$ CFU·$g^{-1}$, $1.1 \times 10^4$ CFU·$g^{-1}$, $8.3 \times 10^5$ CFU·$g^{-1}$, $3.4 \times 10^4$ CFU·$g^{-1}$, $1.4 \times 10^5$ CFU·$g^{-1}$, and $2.5 \times 10^4$ CFU·$g^{-1}$, respectively. At the end of fermentation (40 days) under a salt concentration of 9 g·100 $mL^{-1}$, the contents of *B. subtilis*, *B. halodurans*, *B. megaterium*, *S. saprophytics*, *K. zopfii* and *L. pobuzihii* were $9.5 \times 10^4$ CFU·$g^{-1}$, $2.1 \times 10^4$ CFU·$g^{-1}$, $1.1 \times 10^6$ CFU·$g^{-1}$, $4.4 \times 10^5$ CFU·$g^{-1}$, $2.5 \times 10^5$ CFU·$g^{-1}$, and $3.6 \times 10^4$ CFU $g^{-1}$, respectively. The contents of *B. subtilis*, *B. halodurans*, *B. megaterium*, *S. saprophytics*, *K. zopfii* and *L. pobuzihii* at the end of fermentation under a salt concentration of 18 g·100 $mL^{-1}$ were $2.8 \times 10^2$ CFU·$g^{-1}$, $1.3 \times 10^2$ CFU·$g^{-1}$, $1.6 \times 10^3$ CFU·$g^{-1}$, $1.5 \times 10^2$ CFU·$g^{-1}$, $6.1 \times 10^2$ CFU·$g^{-1}$, and $1.1 \times 10^2$ CFU·$g^{-1}$, respectively. The contents of *B. subtilis*, *B. halodurans*, *B. megaterium*, *S. saprophytics*, *Kurthia* and *L. pobuzihii* at the end of fermentation under a salt concentration of 15 g·100 $mL^{-1}$ were $4.1 \times 10^2$ CFU·$g^{-1}$, $1.4 \times 10^2$ CFU·$g^{-1}$, $1.8 \times 10^2$ CFU·$g^{-1}$, $1.7 \times 10^2$ CFU·$g^{-1}$, $6.3 \times 10^2$ CFU·$g^{-1}$, and $2.4 \times 10^2$ CFU·$g^{-1}$, respectively. The above results show that the contents of spoilage bacteria in the soy sauce prepared by fermentation after reducing the salt concentration of the high-salt dilute-state soy sauce significantly increase.

Example 2

Screening of Strains for Inhibition of Spoilage Bacteria and Identification of their Antibacterial Spectrum (1) Screening of *Weissella*

*Weissella* was isolated by plating serial dilutions of soy sauce mash on a MRS medium containing vancomycin (0.2 g·$L^{-1}$) and natamycin (0.1 g·$L^{-1}$). Soy sauce mash samples were selected on the day 5, day 20 and day 35 of fermentation, 15 g of soy sauce mash was taken and put in a beaker, and 135 mL of sterile normal saline and an appropriate amount of glass beads were added and shaken at 100 r·$min^{-1}$ for 5 min. After standing at room temperature for 5 min, 1 mL of the bacterial suspension was taken, spread after gradient dilution on the MRS medium containing vancomycin (0.2 g·$L^{-1}$) and natamycin (0.1 g·$L^{-1}$), and cultured at 37° C. for 1-3 d, and a single colony was picked for streaking to obtain a pure strain.

(2) Screening of *B. amyloliquefaciens*

5 g of soy sauce mash was taken and put in 100 mL beef extract peptone liquid medium with glass beads and cultured statically at 37° C. for 1-3 d; the upper-layer bacterial solution was subjected to gradient dilution and spread in a beef extract peptone medium, and cultured at 37° C. for 1-3 d; and single colonies were picked for streaking on a beef extract peptone solid medium to obtain single colonies.

(3) Identification of strains

Genomic DNA was extracted from the culture broth of the above strains using a bacterial genomic DNA extraction kit of Tiangen Biotech Co., LTD. The general primers 27F and 1492R of the bacterial 16S rRNA gene were used for PCR amplification, and the PCR products were sent to Talen-Bio Scientific (Wuxi) Co., Ltd. for sequencing. The 16S rRNA gene sequence obtained by sequencing was submitted to GenBank for BLAST comparison and identification of bacterial species.

27F (5'-AGAGTTTGATCCTGGCTCAG-3', SEQ ID NO: 17) and 1492R (5'-GGTTACCTTGTTACGACTT-3', SEQ ID NO: 18)

A PCR reaction system (50 μL): 2 μL of template (50 mg·$L^{-1}$), 1 μL of forward and reverse primers (10 μmol·$L^{-1}$) each, 25 μL of PCR Master Mix, and 21 μL of double distilled water. Reaction conditions: 94° C. for 3 min; 94° C. for 1 min; 55° C. for 1 min; 72° C. for 2 min, 30 cycles; and 72° C. for 10 min. The PCR products were sent to Talen-Bio Scientific (Wuxi) Co., Ltd. for sequencing, and the sequencing results were compared in the NCBI Genbank database. The results showed that *Weissella* was identified as *W. paramesenteroides*, named JL-5; and *Bacillus* was identified as *B. amyloliquefaciens*, named JDF-2.

TABLE 2

Identification of screened strains by BLAST

| Strains | NCBI comparison results | Similarity | 16S rDNA sequences of strains |
|---|---|---|---|
| JDF-2 | B. amyloliquefaciens | 99% | SEQ ID NO: 1 |
| JL-5 | W. paramesenteroides | 99% | SEQ ID NO: 2 |

(4) Verification of the antibacterial activity of isolated strains

Cultivation of strains:

B. subtilis, B. megaterium, B. halodurans, B. amyloliquefaciens, K. zopfii and K. gibosonii were cultured statically at 37° C. in LB medium; W. paramesenteroides, Weissella confusa, Weissella cibaria, T. halophilus and L. pobuzihii were cultured statically at 37° C. in MRS medium; S. saprophytics was cultured statically at 37° C. in nutrient broth medium; and each strain was cultured for 1-2 d.

(1) Preparation of strain fermentation supernatants: B. amyloliquefaciens JDF-2 was inoculated in the LB medium, Weissella and T. halophilus were inoculated in the MRS media, and the strains were cultured at 37° C. and 30° C. respectively to $10^7$ CFU·mL$^{-1}$. An appropriate amount of fermentation broth was taken and centrifuged at 12,000 r·min$^{-1}$ and 4° C. for 5 min, and the supernatants were collected and filtered through a 0.22 μm filter membrane for later use.

(2) Screening of antibacterial microorganisms by an oxford cup method: The indicator bacteria cultured to the logarithmic phase (the bacterial concentration was $10^7$ CFU·mL$^{-1}$) were mixed with soft agar media at 1:50 (v:v), and then the mixtures were poured onto lower-layer media in which oxford cups were placed. After the soft agar were solidified, the oxford cups were taken out, 100 μL of the supernatants of B. amyloliquefaciens JDF-2, W. paramesenteroides JL-5, W. confusa 20, W. cibaria 35, W. paramesenteroides LCW-28 and T. halophilus R44 prepared in step (1) were added to the corresponding wells, and sterile water was added as a control. Then plates were placed in an incubator for culture for 20 h to investigate whether the fermentation of the strains has inhibitory effects on the indicator bacteria. 3 parallels were made for each indicator bacterium. The indicator bacteria were various bacteria derived from soy sauce.

The results are shown in Table 3. W. paramesenteroides JL-5 has a significant inhibitory effect on Bacillus (B. subtilis, B. megaterium and B. halodurans) and S. saprophytic. Among them, the inhibitory effect on B. halodurans was the most obvious, and the diameter of the inhibition zone reached 1.77 cm. B. amyloliquefaciens JDF-2 has the most obvious inhibitory effects on K. zopfii, K. gibsonii and L. pobuzihii.

TABLE 3

Comparison of the inhibition of common spoilages in soy sauce by soy sauce moromi mash isolates

|  | B. subtilis | B. megaterium | B. halodurans | S. saprophytics | K. zopfii | K. gibsonii | L. pobuzihii |
|---|---|---|---|---|---|---|---|
| W. paramesenteroides JL-5 | 1.44* | 1.56 | 1.77 | 0.23 | 0.18 | 0.09 | 0 |
| W. confusa 20 | 0.84 | 0.45 | 1.02 | 0 | 0 | 0 | 0 |
| W. cibaria 35 | 0.55 | 1.21 | 0 | 0.33 | 0 | 0 | 0 |
| W. paramesenteroides LCW-28 | 0.62 | 1.4 | 1.52 | 0 | 0 | 0 | 0 |
| T. halophilus R44 | 0.32 | 0.14 | 0 | 0 | 0 | 0 | 0 |
| B. amyloliquefaciens JDF-2 | 0 | 0 | 0 | 0.22 | 0.54 | 0.42 | 0.25 |

*the data in the table is the diameter of an inhibition zone (cm).

Example 3

Cooperative Fermentation with *Weissella* and *B. amyloliquefaciens* to Prepare High-Salt Dilute-State Salt-Reduced Soy Sauce Cultivation of *W. paramesenteroides*: Single colonies of *W. paramesenteroides* JL-5 screened in Example 2 were picked and inoculated into a MRS medium, cultured statically at 37° C. for 24 h, transferred to a fresh MRS medium at a ratio of 1% (v/v), and cultured at 37° C. until the $OD_{600}$ reached 3.0.

Culture of *B. amyloliquefaciens*: Single colonies of *B. amyloliquefaciens* JDF-2 were picked and inoculated into a liquid LB medium, cultured statically at 37° C. for 24 h, transferred to a fresh LB medium at a ratio of 1% (v/v), and cultured at 37° C. until the $OD_{600}$ reached 3.0.

Culture of *Z. rouxii*: Single colonies of *Z. rouxii* were picked and inoculated into a liquid YPD media, cultured at 30° C. and 220 r·min$^{-1}$ for 30 h, inoculated into a fresh YPD medium at a ratio of 1% (v/v), and cultured until the $OD_{600}$ reached 4.0.

Low-salt dilute-state soy sauce fermentation process:

(1) Koji making process: Defat soybeans were steamed at 121° C. (0.1 MPa) for 20 min, uniformly mixing the cooled soybean with wheat flour at a mass ratio of (4-6):1, a soy sauce koji starter accounting for 1.5% of the total mass of the mixed raw materials was added and uniformly mixed, the mixture was cultured at 30° C., the koji was turned at the right time, and the finished koji was prepared after 48 h when the surface of the koji is covered with yellow-green hyphae.

(2) Fermentation process: The finished koji prepared in step (1) was mixed with NaCl brine at a volume ratio of 1:2.5, *Z. rouxii* ZQ01 ($10^7$ CFU·g$^{-1}$) was added on day 3-day 5, and the mixture was fermented at 30° C. for 40 days while being stirred once a day during fermentation.

A total of 6 groups of soy sauce mash were set up for fermentation, as follows:

(a) Group A: the salt concentration of the soy sauce mash mixed with the brine in step (2) was controlled at 18 g·100 mL$^{-1}$;

(b) Group B: the salt concentration of the soy sauce mash mixed with the brine in step (2) was controlled at 12 g·100 mL$^{-1}$;

(c) Group C: the salt concentration of the soy sauce mash mixed with the brine in step (2) was controlled at 12 g·100 mL$^{-1}$, and *W. paramesenteroides* JL-5 with a final concentration of $1.0 \times 10^7$ CFU·g$^{-1}$ was added to the soy sauce mash system;

(d) Group D: the salt concentration of the soy sauce mash mixed with the brine in step (2) was controlled at 12 g·100 mL$^{-1}$, and *B. amyloliquefaciens* JDF-2 with a final concentration of $1.0 \times 10^7$ CFU·g$^{-1}$ was added to the soy sauce mash system;

(e) Group E: the salt concentration of the soy sauce mash mixed with the brine in step (2) was controlled at 12 g·100 mL$^{-1}$, and *W. paramesenteroides* JL-5 with a final concentration of $1.0 \times 10^7$ CFU·g$^{-1}$ and *B. amyloliquefaciens* JDF-2 with a final concentration of $1.0 \times 10^7$ CFU·g$^{-1}$ were added to the soy sauce mash system; and (f) Group F: the salt concentration of the soy sauce mash mixed with the brine in step (2) was controlled at 12 g·100 mL$^{-1}$, the addition of *Z. rouxii* was omitted, and *W. paramesenteroides* JL-5 with a final concentration of $1.0 \times 10^7$ CFU·g$^{-1}$ and *B. amyloliquefaciens* JDF-2 with a final concentration of $1.0 \times 10^7$ CFU·g$^{-1}$ were added to the soy sauce mash system.

The physicochemical indexes of the soy sauce samples in the groups A-F were detected. The results show that: Groups A and E can make the amino acid nitrogen content reach 1.2 g·100 mL$^{-1}$ and 1.16 g·100 mL$^{-1}$, and the total acid content reach 8.1 g·L$^{-1}$ and 7.5 g·L$^{-1}$. The amino acid nitrogen contents of Groups C and F can reach 1.08 g·100 mL$^{-1}$ and 1.04 g·100 mL$^{-1}$ respectively, and the amino acid nitrogen content of Group D is relatively low, only 0.85 g·100 mL$^{-1}$. However, the fermented soy sauces of the above groups all meet the Chinese Hygienic Standard for Soy Sauce GB2717-2018 and the Japanese Quality Standard for Soy Sauce G/TBT/N/JPN/297. The amino acid nitrogen content of Group B is 0.38 g·100 mL$^{-1}$, which does not meet the Chinese Hygienic Standard for Soy Sauce GB2717-2018 and the Japanese Quality Standard for Soy Sauce G/TBT/N/JPN/297.

Figure 8:
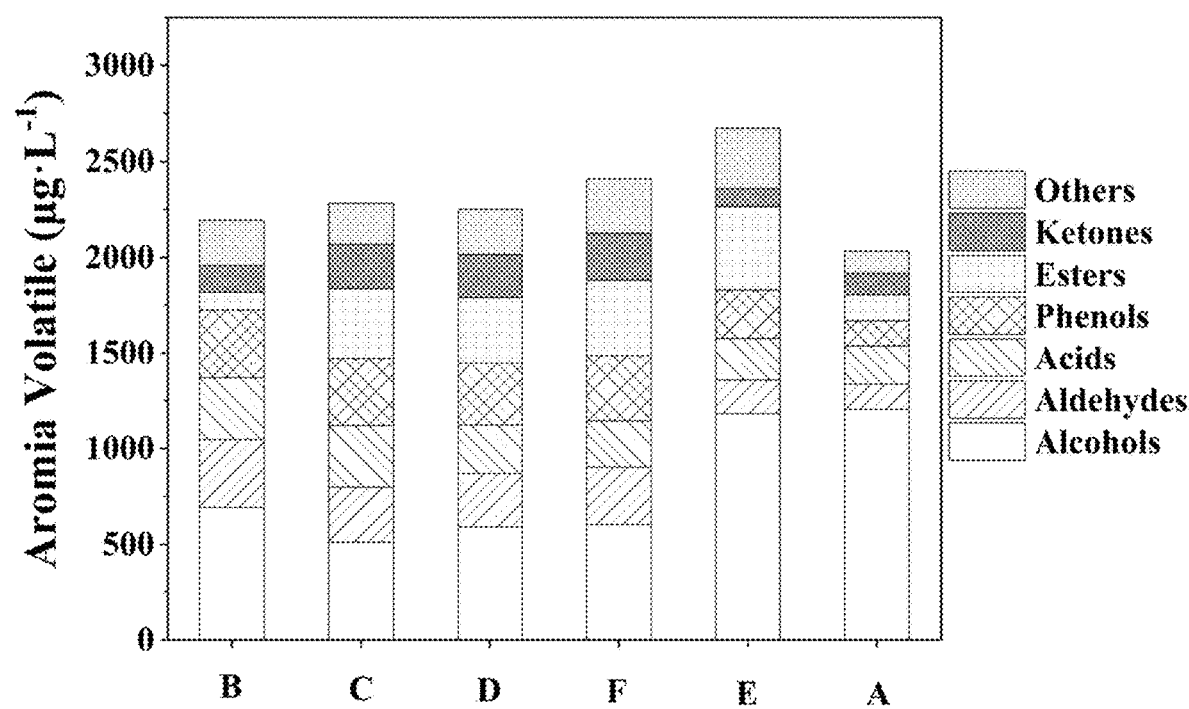
FIG. 8 shows the content of volatiles in the soy sauce produced by different fermentation methods.

The contents of volatiles in soy sauce samples with different strain addition methods were detected, and the results are shown in FIG. 8: the total content of flavor substances in Group E was 2674.39 μg·L$^{-1}$, which was increased by 20.64% compared with that in Group B; the content of esters was 437.72 μg·L$^{-1}$, which was 3.74 times higher than that in Group B; and the content of alcohols was 1181.66 μg·L$^{-1}$, which was 70.72% higher than that in Group B. This indicates that the *W. paramesenteroides* JL-5 and the *B. amyloliquefaciens* JDF-2 can jointly promote the formation of volatiles in soy sauce. The contents of volatiles of Group C with the *W. paramesenteroides* JL-5 added alone and Group D with the *B. amyloliquefaciens* JDF-2 added alone were 2283.84 μg·L$^{-1}$ and 2252.86 μg·L$^{-1}$ respectively, and compared with group B, the contents of esters were increased by 2.9 times and 2.7 times respectively, but the contents of alcohols were reduced by 26% and 14.4% respectively. In the soy sauce fermented in Group F, the total content of volatiles was increased to 2430.7 μg·L$^{-1}$, the content of esters was increased by 3.3 times, and the content of alcohols was decreased by 9.7%.

The biogenic amine contents in soy sauce samples with different addition methods were detected, and the results showed that compared with Group B, the total biogenic amine content in Group E was 93.365 mg·L$^{-1}$, which was decreased by 84.65%, wherein the contents of histamine and tyramine were 21.21 mg·L$^{-1}$ and 12.332 mg·L$^{-1}$, which were decreased by 90.06% and 92.53% respectively. The total biogenic amine contents in Group C and Group F were 179.8 mg·L$^{-1}$ and 216.1 mg·L$^{-1}$ respectively, which were reduced by 70.6% and 64.7% respectively compared with Group B.

Example 4

Application of *W. paramesenteroides* to Inhibit Spoilage Bacteria in a Simulated Soy Sauce Fermentation System Miscellaneous bacteria and spoilage bacteria (*B. subtilis, B. megaterium, B. halodurans, S. saprophytics, L. pobuzihii* and *K. zopfii*) were combined with equal amount and added in the soy sauce mash fermentation medium (supplemented with salt 10-12 g·100 mL$^{-1}$) with a total concentration of $1.0 \times 10^6$ CFU·mL$^{-1}$, for simulated soy sauce fermentation. Then, the strains capable of inhibiting the growth of the spoilage bacteria were inoculated into the simulated fermentation systems by the following methods to verify the conditions that the strains inhibit the growth of the spoilage bacteria in the systems.

Strain addition methods:

(1) *W. paramesenteroides* JL-5 and *B. amyloliquefaciens* JDF-2 were added at a final concentration of $1.0 \times 10^7$ CFU·g$^{-1}$ at a ratio of bacterial cell numbers of 1:1.

(2) *T. halophilus* R44 was added separately at a final concentration of $1.0 \times 10^7$ CFU·g$^{-1}$; and the *T. halophilus* R44 was disclosed in the paper "Effect of Enrichment Tetragenococcus halophilus on Simulated Fermentation of Low-Salt Soy Sauce" published in 2020.

(3) *W. paramesenteroides* LCW-28 was added separately at a final concentration of $1.0 \times 10^7$ CFU·g$^{-1}$; and the *W. paramesenteroides* LCW-28 was disclosed in the patent "Method for Increasing Content of Flavor Substances in Soy Sauce" published in 2020.

(4) *W. cibaria* 35 and *W. confusa* 20 were added separately at a final concentration of $1.0 \times 10^7$ CFU·g$^{-1}$; and the *W. cibaria* 35 and *W. confusa* 20 were disclosed in the paper "Detection of Characteristics of *Weissella* Strains and Their Contents in Soy Sauce Moromi Mash during Soy Sauce Fermentation" published in 2018.

The results are shown in FIG. 5. When *W. paramesenteroides* JL-5 was added alone, on day 20 of fermentation, the number of *B. megaterium, B. subtilis, B. halodurans* and *S. saprophytics* in simulated fermentation mash were $1.2 \times 10^3$ CFU·g$^{-1}$, $6.3 \times 10^3$ CFU·g$^{-1}$, $1.1 \times 10^4$ CFU·g$^{-1}$ and $1.3 \times 10^3$ CFU·g$^{-1}$, respectively. And compared with the control group, the above spoilage bacteria were significantly inhibited, but the numbers of *K. zopfii* and *L. pobuzihii* were not significantly reduced.

When the *B. amyloliquefaciens* JDF-2 was added alone, *L. pobuzihii* and *K. zopfii* in the fermentation system can be significantly inhibited, and the bacterial cell concentrations were reduced to $1.0 \times 10^4$ CFU·g$^{-1}$ and $2.3 \times 10^5$ CFU·g$^{-1}$ on day 20 of fermentation, respectively. The *B. amyloliquefaciens* JDF-2 has no significant inhibitory effect on other spoilage bacteria and miscellaneous bacteria.

Co-inoculation of the *W. paramesenteroides* JL-5 and the *B. amyloliquefaciens* JDF-2 could significantly inhibit the growth of 6 types of spoilage bacteria, and on day 20 of fermentation, the contents of *B. megaterium, B. subtilis, B. halodurans, S. saprophytics, K. zopfii* and *L. pobuzihii* were reduced to $1.0 \times 10^3$ CFU·g$^{-1}$, $6.1 \times 10^3$ CFU·g$^{-1}$, $6.7 \times 10^3$ CFU·g$^{-1}$, $1.0 \times 10^3$ CFU·g$^{-1}$, $8.2 \times 10^3$ CFU·g$^{-1}$ and $5.3 \times 10^3$ CFU g$^{-1}$, respectively.

Example 5

Preparation of High-Salt Dilute-State Soy Sauce Fermentation with Reduced-Salt Content by using *Weissella* and/or *B. amyloliquefaciens*

Koji making process: Defat soybeans were steamed at 121° C. (0.1 MPa) for 20 min., uniformly mixing the cooled soybean with wheat flour at a mass ratio of (4-6):1, a soy sauce koji starter accounting for 1.5% of the total mass of the raw materials was added and mixed, the mixture was cultured at 30° C. for 40-48 h until the surface of the koji was covered with yellow-green hyphae.

Fermentation process: The finished koji was mixed with brine containing 150-250 g·L$^{-1}$ NaCl at a volume ratio of 1:(2-3). The mixed soy sauce mash was fermented, wherein the final salt concentration in the system reached 10-12 g·100 mL$^{-1}$, and fermenting was performed at 30° C. for 40-60 days. The soy sauce mash was stirred once a day in the early stage of fermentation and twice a week in the later stage of fermentation.

Addition of strains: *W. paramesenteroides* JL-5 and *B. amyloliquefaciens* JDF-2 were added to the soy sauce mash with an inoculation size of 3%-5%, so that the bacterial cell number after inoculation was greater than $1 \times 10^7$ CFU·g$^{-1}$. When the pH of the soy sauce mash was 5.0-5.5, *Z. rouxii* was added with an inoculation size of 3%, so that the yeast cell number was greater than $1 \times 10^8$ CFU·g$^{-1}$.

Criteria for physiochemical properties of soy sauce mash and bacteria population: The number of spoilage bacteria (*B. subtilis, B. megaterium, B. halodurans, K. zopfii, L. pobuzihii* and *S. saprophytics*) should be less than or equal to $1.0 \times 10^4$ CFU·g$^{-1}$, the amino acid nitrogen content was controlled to be greater than or equal to 1 g·100 mL$^{-1}$, the total acid content was less than or equal to 12 g·L$^{-1}$, and the pH was controlled at 5-5.5.

The finished product after fermentation had an amino acid nitrogen content of greater than or equal to 1.2 g·100 mL$^{-1}$, contents of various spoilage bacteria of less than $1.0 \times 10^3$ CFU·g$^{-1}$, a NaCl concentration of 10 g-12 g·100 mL$^{-1}$, and a sodium content of 380 mg -420 mg·10 mL$^{-1}$.

Example 6

Application of *W. paramesenteroides* and *B. amyloliquefaciens* to Improve the Quality Stability in the Shelf Life of Low-Salt Soy Sauce Soy sauce were prepared according to the methods of Example 3, and the soy sauce were divided into 4 groups according to the following methods, namely:

Group a: a soy sauce with an initial fermentation salt concentration of 12 g·100 mL$^{-1}$ was prepared according to the method of Group B in Example 3;

Group b: potassium sorbate with a final concentration of 1 g·L$^{-1}$ was added on the basis of the soy sauce prepared in Group a;

Group c: a soy sauce with an initial fermentation salt concentration of 18 g·100 mL$^{-1}$ was prepared according to the method of Group A in Example 3; and Group d: a soy sauce was prepared according to the method of Group E in Example 3.

After the fermentation, the soy sauce mash was squeezed and filtered with gauze to obtain crude soy sauce. The crude soy sauce samples were sterilized at 121° C. for 20 min, and aseptically transferred into 1 L sterile glass bottles, and the bottles were sealed and placed at room temperature for 0-60 d. Samples were taken on day 0, day 10, day 30, and day 60.

According to the Chinese Hygienic Standard for Soy Sauce (GB2717-2018), the total number of bacteria in soy sauce shall be less than $5 \times 10^3$ CFU·mL$^{-1}$, and the coliform group shall be less than 10 CFU·mL$^{-1}$. The results showed that: on day 10 of storage, the total number of bacteria in Group a was $3.2 \times 10^4$ CFU·mL$^{-1}$, which did not meet the hygienic standards for soy sauce. On day 30 of storage, the total number of bacteria in Group a reached $6.8 \times 10^7$ CFU·mL$^{-1}$, which exceeded the hygienic standards for soy sauce by 4 orders of magnitude; Group b reached $4.1 \times 10^4$ CFU·mL$^{-1}$, which did not meet the hygienic standards for soy sauce; and both Group c and d met the hygienic standards for soy sauce. On day 60 of storage, the total numbers of bacteria in Groups c and d were both lower than $5 \times 10^3$ CFU·mL$^{-1}$, which met the hygienic standards for soy sauce; and the total number of colonies in Group a was $6.2 \times 10^9$ CFU·mL$^{-1}$, and Group b reached $3.5 \times 10^5$ CFU·mL$^{-1}$, both of which exceeded the hygienic standards for soy sauce. The above results confirm that the low-salt soy sauce produced by synergistic fermentation with the *W. paramesenteroides* JL-5 and the *B. amyloliquefaciens* JDF-2 maintains good and stable quality in the shelf life without adding any preservatives, which is of great significance to prolong the shelf life of low-salt soy sauce without preservatives. When the soy sauce prepared by this method was stored for 60 days, the total number of microorganisms was not significantly different from that of a high-salt dilute-state soy sauce, which met the hygienic standards for soy sauce. The low-salt soy sauce with *W. paramesenteroides* JL-5 and *B. amyloliquefaciens* JDF-2 added for cooperative fermentation in this patent has better quality stability in the shelf life than the low-salt soy sauce with preservatives.

TABLE 4

Microbial changes in low-salt soy sauce at different storage times

| Storage Group | 0 d | | 10 d | | 30 d | | 60 d | |
|---|---|---|---|---|---|---|---|---|
| | Total number of bacteria (CFU·mL$^{-1}$) | Coliform (CFU·mL$^{-1}$) | Total number of bacteria (CFU·mL$^{-1}$) | Coliform (CFU·mL$^{-1}$) | Total number of bacteria (CFU·mL$^{-1}$) | Coliform (CFU·mL$^{-1}$) | Total number of bacteria (CFU·mL$^{-1}$) | Coliform (CFU·mL$^{-1}$) |
| a | 0 | 0 | $6.1 \times 10^4$ | $1.1 \times 10^2$ | $6.8 \times 10^7$ | $2.2 \times 10^2$ | $6.2 \times 10^9$ | $1.8 \times 10^3$ |
| b | 0 | 0 | $1.3 \times 10^2$ | 9 | $4.1 \times 10^4$ | 13 | $3.5 \times 10^5$ | 28 |
| c | 0 | 0 | 23 | 8 | 95 | 11 | $2.8 \times 10^2$ | 18 |
| d | 0 | 0 | 18 | 5 | 65 | 8 | $2.3 \times 10^2$ | 20 |

Although the present disclosure has been disclosed as above in preferred examples, it is not intended to limit the present disclosure. Anyone skilled in the art can make various changes and modifications without departing from the spirit and scope of the present disclosure. Therefore, the protection scope of the present disclosure should be defined by the claims.

---

What is claimed is:

1. A method for producing high-salt dilute-state soy sauce, comprising cooking, koji making, and fermentation;

the fermentation comprising: mixing finished koji with brine at a volume ratio of 1:(2-3), so that the final concentration of salt in the system is less than or equal to 12 g·100 mL$^{-1}$, adding *Weissella paramesenteroides* (*W. paramesenteroides*) JL-5 and *Bacillus amyloliquefaciens* (*B. amyloliquefaciens*) JDF-2, or a composition containing the *W. paramesenteroides* JL-5 and the *B. amyloliquefaciens* JDF-2, and performing fermentation at 25-30° C. for at least 30 days;

wherein the *W. paramesenteroides* JL-5 is maintained in the China Center for Type Culture Collection, with a preservation number of CCTCC NO: M 2021707; and wherein the *B. amyloliquefaciens* JDF-2 is maintained in the China Center for Type Culture Collection, with a preservation number of CCTCC NO: M 2021737.

2. The method according to claim 1, wherein the concentration of the *W. paramesenteroides* JL-5 is greater than or equal to $1.0×10^7$ CFU·g$^{-1}$, and the concentration of the *B. amyloliquefaciens* JDF-2 is greater than or equal to $1.0×10^6$ CFU·g$^{-1}$.

3. The method according to claim 1, wherein the finished koji is prepared by a method comprising: steaming defatted soybeans at 121° C. (0.1 MPa) for 20 min., uniformly mixing cooled soybean with wheat flour at a mass ratio of (4-6):1, adding a soy sauce koji starter accounting for 1-1.5% of the total mass of the mixed raw materials, performing uniform mixing, and performing culturing at 28° C.-30° C., wherein the koji making process takes 40 hours-48 hours.

4. The method according to claim 1, wherein the composition is a starter containing the *W. paramesenteroides* JL-5 and the *B. amyloliquefaciens* JDF-2, wheat koji, bran koji or other types of koji for fermentation.

5. The method according to claim 1, comprising the following steps:

(1) koji making process: steaming defatted soybeans at 121° C. (0.1 MPa) for 20 min., uniformly mixing the cooled soybean with wheat flour at a mass ratio of (4-6):1, adding a soy sauce koji starter accounting for 1-1.5% of the total mass of the mixed raw materials, performing uniform mixing, and performing culturing at 28° C.-30° C., wherein the koji making process takes 40 hours-48 hour; and (2) fermentation process: mixing the finished koji prepared in step (1) with brine containing NaCl at a volume ratio of 1:(2-3), so that the final concentration of salt in the system is less than or equal to 12 g·100 mL$^{-1}$, adding the *W. paramesenteroides* JL-5 and the *B. amyloliquefaciens* JDF-2, or adding the starter, wheat koji, bran koji or other types of koji for fermentation, and performing fermentation at 25° C.-30° C. for 40 days; during fermentation, on day 3 to day 5, adding *Zygosaccharomyces rouxii* ZQ01, and performing stirring during the fermentation.

6. The method according to claim 5, wherein the concentration of the *W. paramesenteroides* JL-5 in a soy sauce mash containing salt with a concentration of 12 g·100 mL$^{-1}$ is at least $1.0×10^7$ CFU·g$^{-1}$.

7. The method according to claim 5, wherein the number of the *W. paramesenteroides* JL-5 added and the number of the *B. amyloliquefaciens* JDF-2 added are in a same order of magnitude.

8. The method according to claim 5, wherein the method makes the produced soy sauce have at least one of the following features (a)-(e):

(a) the number of spoilage bacteria in the produced soy sauce is reduced compared to a control soy sauce not made by the method;

(b) the salt content in the produced soy sauce is less than or equal to 12 g·100 mL$^{-1}$;

(c) the biogenic amine content in the produced soy sauce is reduced compared to a control soy sauce not made by the method;

(d) the stability during the shelf life of the produced soy sauce is improved compared to a control soy sauce not made by the method; and (e) the formation of volatiles in the produced soy sauce is promoted.

9. The method according to claim 8, wherein the spoilage bacteria comprise at least one of: *Bacillus subtilis, Bacillus halodurans, Bacillus megaterium, Staphylococcus saprophytics, Kurthia zopfii, Kurthia gibsonii,* and *Lactobacillus pobuzihii*.

10. A starter containing *Weissella paramesenteroides* JL-5 and/or *Bacillus amyloliquefaciens* JDF-2, wheat koji, bran koji or other types of koji for fermentation, wherein the *W. paramesenteroides* JL-5 is maintained in the China Center for Type Culture Collection, with a preservation number of CCTCC NO: M 2021707; and the *B. amyloliquefaciens* JDF-2 is maintained in the China Center for Type Culture Collection, with a preservation number of CCTCC NO: M 2021737.

* * * * *

SEQUENCE LISTING

<160> NUMBER OF SEQ ID NOS: 18

<210> SEQ ID NO 1
<211> LENGTH: 1407
<212> TYPE: DNA
<213> ORGANISM: Bacillus amyloliquefaciens

<400> SEQUENCE: 1

```
atgaataaag ctttgaaagc gctcggcgtg ctgacgacgt tcgttatgct cgtcgtgctg      60
atcggcggcg ctcttgtcac aaaaacagga tcgggtctcg gttgcggaag gcagtggccg     120
ctttgccacg gccggttttt cccggagctt aacgccgctt ctattattga atggagccac     180
agactcgcaa gcggtgtctc aatcgttctc gtgctgagtc tcgcttttg ggcatggaga      240 aaagtcacgc ctgttttccg tgaaacaacc tttctcgcca ttatgtccat tatcttttta     300
tttttacagg cgcttctcgg cgcattagcg gttgttttcg gatcaaatgc gctcgttatg     360
gcgcttcatt tcggcatatc gctgatttct ttcgcttctg ttctgatttt gacgcttctc     420
atatttgaag ctgataaatc agacaaaaag ctcgtcaagc cgctcagaat cggcaggaaa     480
atgcagtttc atatgatcgg cctttcgatt tacacgtata tcgtcgttta tcgggggct      540 tatgtgcgcc atacgaaatc aagccttgcc tgccctgacg ttccgctttg cagcaggctg     600
aaccacgggt ttccgtctca ttttcaggaa tgggtgcaga tgggccacag aacggcagcg     660
ctgcttctgt tcgtatggat tcttgtcgct tttgcgcatg cggtgcgctc ctacaaagac     720
caaaaacaga ttcttggggg ctggatagcg gctcttgcct tgttgtatt acaggcgctg      780 tccggaatca tggttgttta ttcagaaatg gccaccggct ttgcacttgc ccattcgctc     840
tttattgccg gtctgttcgg cgtcttatgc tatttcttat tattaatcgc ccgcttccgc     900
tatgaatcaa aacagcggaa cgtctgaatg atcaatcgtc aacatattca attatcgctg     960
cagtctttaa gcttagtggc agggtttatg gtgtgggtgc tgatttcatc gctcatttct    1020
caaatgacat cagatattca tttaagcaaa ggcgagattt cattggtgac ggcgattccc    1080
gttattctcg gatcgcttct ccgtattcct ttaggatatt taacgaacag gtatggcgcg    1140
cggctgatgt ttatgatcag cttcatcctg cttttgtttc ccgtattttg gatcagtatc    1200
```

-continued

```
gcggattctt tatttgattt aatcacgggc ggcttttttct tagggatcgg cggagcggta    1260
ttctccatcg gagtgacgtc cctcccgaaa tattatccga aagaaaagca cggtgtcgtc    1320
aatgggattt acggtgccgg aaacatcggg accgccgtta ctacctttgc ggcgccggtt    1380
atcgctcaag ccgcgggatg gaaagca                                         1407
```

<210> SEQ ID NO 2
<211> LENGTH: 900
<212> TYPE: DNA
<213> ORGANISM: Weisellas paramesenteroides

<400> SEQUENCE: 2

```
atgggatatg gcggcagcta taatgcagtc gaacgctttg tctttaattg atatgacgag     60
cttgctctga tttgatttta tctgacaaag agtggcgaac gggtgagtaa cacgtgggta    120
acctacctct tagcagggga taacatttgg aaacaagtgc taataccgta aataccaac    180 aaccgcatgg ttgttggttg aaagatggtt ctgctatcac taagagatgg acccgcggtg    240
cattagctag ttggtaaggt aacggcttac caaggcaatg atgcatagcc gagttgagag    300
actgatcggc cacaatggga ctgagacacg gcccatactc ctacgggagg cagcagtagg    360
gaatcttcca caatgggcgc aagcctgatg gagcaacgcc gcgtgtgtga tgaagggttt    420
cggctcgtaa aacactgtta taagagaaga acggcactga gggtaactgt tcagtgtgtg    480
acggtatctt accagaaagg aacggctaaa tacgtgccag cagccgcggt aatacgtatg    540
ttccaagcgt tatccggatt tattgggcgt aaagcgagcg cagacggtta tttaagtctg    600
aagtgaaagc cctcagctca actgaggaat ggctttggaa actggatgac ttgagtgcag    660
tagaggaaag tggaactcca tgtgtagcgg tgaaatgcgt agatatatgg aagaacacca    720
gtggcgaagg cggctttctg gactgtaact gacgttgagg ctcgaaagtg tgggtagcaa    780
acaggattag ataccctggt agtccacacc gtaaacgatg agtgctagat gttcgagggt    840
ttccgccctt gagtgtcgca gctaacgcat taagcactcc gctggggagt acgaccgcaa    900
```

<210> SEQ ID NO 3
<211> LENGTH: 21
<212> TYPE: DNA
<213> ORGANISM: artificial sequence
<220> FEATURE:
<223> OTHER INFORMATION: synthetic DNA

<400> SEQUENCE: 3

```
ctggatcacg gtttacttca c                                                21
```

<210> SEQ ID NO 4
<211> LENGTH: 21
<212> TYPE: DNA
<213> ORGANISM: artificial sequence
<220> FEATURE:
<223> OTHER INFORMATION: synthetic DNA

<400> SEQUENCE: 4

```
ccattaccat caatacctgc a                                                21
```

<210> SEQ ID NO 5
<211> LENGTH: 20
<212> TYPE: DNA
<213> ORGANISM: artificial sequence
<220> FEATURE:
<223> OTHER INFORMATION: synthetic DNA

<400> SEQUENCE: 5

-continued

```
acttactttc caaatgtcga                                           20

<210> SEQ ID NO 6
<211> LENGTH: 20
<212> TYPE: DNA
<213> ORGANISM: artificial sequence
<220> FEATURE:
<223> OTHER INFORMATION: synthetic DNA

<400> SEQUENCE: 6
tcgttctaag tatggtgcga                                           20

<210> SEQ ID NO 7
<211> LENGTH: 20
<212> TYPE: DNA
<213> ORGANISM: artificial sequence
<220> FEATURE:
<223> OTHER INFORMATION: synthetic DNA

<400> SEQUENCE: 7
caattataat taactaaggt                                           20

<210> SEQ ID NO 8
<211> LENGTH: 20
<212> TYPE: DNA
<213> ORGANISM: artificial sequence
<220> FEATURE:
<223> OTHER INFORMATION: synthetic DNA

<400> SEQUENCE: 8
ttacaaggga atcattaact                                           20

<210> SEQ ID NO 9
<211> LENGTH: 19
<212> TYPE: DNA
<213> ORGANISM: artificial sequence
<220> FEATURE:
<223> OTHER INFORMATION: synthetic DNA

<400> SEQUENCE: 9
tcattacaaa tataacaag                                            19

<210> SEQ ID NO 10
<211> LENGTH: 19
<212> TYPE: DNA
<213> ORGANISM: artificial sequence
<220> FEATURE:
<223> OTHER INFORMATION: synthetic DNA

<400> SEQUENCE: 10
agcttgttct actgtatcc                                            19

<210> SEQ ID NO 11
<211> LENGTH: 22
<212> TYPE: DNA
<213> ORGANISM: artificial sequence
<220> FEATURE:
<223> OTHER INFORMATION: synthetic DNA

<400> SEQUENCE: 11
tcagaactca gcgaaatcga ga                                        22

<210> SEQ ID NO 12
<211> LENGTH: 21
<212> TYPE: DNA
```

```
<213> ORGANISM: artificial sequence
<220> FEATURE:
<223> OTHER INFORMATION: synthetic DNA

<400> SEQUENCE: 12
ctatataagg agaggaatgg t                                              21

<210> SEQ ID NO 13
<211> LENGTH: 21
<212> TYPE: DNA
<213> ORGANISM: artificial sequence
<220> FEATURE:
<223> OTHER INFORMATION: synthetic DNA

<400> SEQUENCE: 13
tttggtggcg atagcgaaga g                                              21

<210> SEQ ID NO 14
<211> LENGTH: 19
<212> TYPE: DNA
<213> ORGANISM: artificial sequence
<220> FEATURE:
<223> OTHER INFORMATION: synthetic DNA

<400> SEQUENCE: 14
gagtaggacg ctgccaagc                                                 19

<210> SEQ ID NO 15
<211> LENGTH: 22
<212> TYPE: DNA
<213> ORGANISM: artificial sequence
<220> FEATURE:
<223> OTHER INFORMATION: synthetic DNA

<400> SEQUENCE: 15
accgcgttcg cctcattgaa ca                                             22

<210> SEQ ID NO 16
<211> LENGTH: 21
<212> TYPE: DNA
<213> ORGANISM: artificial sequence
<220> FEATURE:
<223> OTHER INFORMATION: synthetic DNA

<400> SEQUENCE: 16
agcgctccaa gcgctagcac g                                              21

<210> SEQ ID NO 17
<211> LENGTH: 20
<212> TYPE: DNA
<213> ORGANISM: artificial sequence
<220> FEATURE:
<223> OTHER INFORMATION: synthetic DNA

<400> SEQUENCE: 17
agagtttgat cctggctcag                                                20

<210> SEQ ID NO 18
<211> LENGTH: 19
<212> TYPE: DNA
```

```
<213> ORGANISM: artificial sequence
<220> FEATURE:
<223> OTHER INFORMATION: synthetic DNA

<400> SEQUENCE: 18
ggttaccttg ttacgactt                                               19
```